United States Patent
Huang et al.

(10) Patent No.: US 11,680,099 B2
(45) Date of Patent: Jun. 20, 2023

(54) ANTI-PD-1/CD47 BISPECIFIC ANTIBODY AND APPLICATION THEREOF

(71) Applicant: HANX BIOPHARMACEUTICS, INC, Hubei (CN)

(72) Inventors: Ying Huang, Hubei (CN); Faming Zhang, Hubei (CN); Gan Xi, Hubei (CN)

(73) Assignee: HANX BIOPHARMACEUTICS, INC, Wuhan (CN)

(*) Notice: Subject to any disclaimer, the term of this patent is extended or adjusted under 35 U.S.C. 154(b) by 228 days.

(21) Appl. No.: 16/892,912

(22) Filed: Jun. 4, 2020

(65) Prior Publication Data

US 2020/0291118 A1    Sep. 17, 2020

Related U.S. Application Data

(63) Continuation of application No. PCT/CN2017/115323, filed on Dec. 8, 2017.

(51) Int. Cl.
| | |
|---|---|
| C07K 16/28 | (2006.01) |
| A61P 35/00 | (2006.01) |
| A61K 39/00 | (2006.01) |
| C07K 14/705 | (2006.01) |
| C12N 15/86 | (2006.01) |

(52) U.S. Cl.
CPC .......... C07K 16/2818 (2013.01); A61P 35/00 (2018.01); C07K 14/70596 (2013.01); C12N 15/86 (2013.01); A61K 2039/505 (2013.01); C07K 2317/31 (2013.01); C07K 2317/56 (2013.01); C07K 2319/00 (2013.01)

(58) Field of Classification Search
CPC .......... C07K 16/2818; C07K 14/70596; C07K 2317/31; C07K 2317/56; C07K 2319/00; A61P 35/00; A61K 2039/505; C12N 15/86
See application file for complete search history.

(56) References Cited

U.S. PATENT DOCUMENTS

| | | | |
|---|---|---|---|
| 2017/0101470 A1* | 4/2017 | Liu | A61K 47/22 |
| 2017/0233808 A1* | 8/2017 | Haining | C12Q 1/6883 |
| | | | 424/85.4 |

FOREIGN PATENT DOCUMENTS

| | | | |
|---|---|---|---|
| CN | 106456749 A | 2/2017 | |
| CN | 107286242 A | 10/2017 | |
| JP | 2017510249 A | 4/2017 | |
| JP | 2017510251 A | 4/2017 | |
| JP | 2017525698 A | 9/2017 | |
| WO | WO-2013109752 A1 * | 7/2013 | ............. A61P 35/00 |
| WO | 2016024021 A1 | 2/2016 | |
| WO | 2017127707 A1 | 7/2017 | |
| WO | 2017166804 A1 | 10/2017 | |

OTHER PUBLICATIONS

Casset et al, Biochemical and Biophysical Research Communications, 2003, 307:198-205 (Year: 2003).*
Rudikoff et al, Proceedings of the National Academy of Sciences, 1982, 79:1979-1983 (Year: 1982).*
MacCallum et al, Journal of Molecular Biology, 1996, 262:732-745 (Year: 1996).*
Holm et al, Molecular Immunology, 2007:1075-1084 (Year: 2007).*
Chen et al, Journal of Molecular Biology, 1999, 293:865-881 (Year: 1999).*
Office Action issued for JP patent application serial No. 2020-531011, dated Jun. 22, 2021, with English translation.
Search Report issued for EP patent application serial No. 17934019.5, dated Jun. 23, 2021.
Yanagita, T., et al. "Anti-SIRPα antibodies as a potential new tool for cancer immunotherapy" JCI Insight (2017) 2(1), p. 1-15: e89140.
Tao, Hua et al. "Targeting CD47 Enhances the Efficacy of Anti-PD-1 and CTLA-4 in an Esophageal Squamous Cell Cancer Preclinical Model" Oncology Research Featuring Preclinical and Clinical Cancer Therapeutics, vol. 25, No. (9), Nov. 2, 2017 (Nov. 2, 2017), pp. 1579-1587.
Yu, Guangtao et al. "PD-1 Blockade Attenuates Immunosuppressive Myeloid Cells Due to Inhibition of CD47/SIRPα Axix in HPV Negative Head and Neck Squamous Cell Carcinoma" Oncotarget, vol. 6, No. (39), Nov. 7, 2015 (Nov. 7, 2015), pp. 42067-42080.
International Search Report issued for PCT/CN2017/115323, dated Sep. 7, 2018.
Written Opinion of the International Searching Authority issued for PCT/CN2017/115323, dated Sep. 7, 2018.

* cited by examiner

Primary Examiner — Mark Halvorson
Assistant Examiner — Dennis J Sullivan
(74) Attorney, Agent, or Firm — Westman, Champlin & Koehler, P.A.; Z. Peter Sawicki

(57) ABSTRACT

The present invention provides a recombinant protein. The recombinant protein includes an anti-PD-1 antibody and human SIRPA extracellular domain. The N-terminus of the human SIRPA extracellular domain is linked to the C-terminus of the heavy chain of the anti-PD-1 antibody.

10 Claims, 8 Drawing Sheets

Specification includes a Sequence Listing.

SEQUENCE LISTING

<160> NUMBER OF SEQ ID NOS: 10

<210> SEQ ID NO 1
<211> LENGTH: 17
<212> TYPE: PRT
<213> ORGANISM: Artificial Sequence
<220> FEATURE:
<223> OTHER INFORMATION: amino acid sequence of linker

<400> SEQUENCE: 1

Gly Gly Gly Gly Ser Gly Gly Gly Ser Glu Arg Gly Glu Thr Gly
1               5                   10                  15

Pro

<210> SEQ ID NO 2
<211> LENGTH: 218
<212> TYPE: PRT
<213> ORGANISM: Artificial Sequence
<220> FEATURE:
<223> OTHER INFORMATION: amino acid sequence of light chain of
      recombinant protein

<400> SEQUENCE: 2

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Lys Gly Thr Gly Val Pro Ala
    50                  55                  60

Arg Phe Ser Gly Ser Gly Ser Gly Thr Asp Phe Thr Leu Asn Ile Asn
65                  70                  75                  80

Pro Met Glu Glu Glu Asp Thr Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 580
<212> TYPE: PRT
<213> ORGANISM: Artificial Sequence
<220> FEATURE:
<223> OTHER INFORMATION: amino acid sequence of polypeptide of
      recombinant protein

<400> SEQUENCE: 3

Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Ala Pro Gly Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Gln Lys Gly Glu Ala Trp Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

```
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys Gly Gly Gly
        435                 440                 445
Gly Ser Gly Gly Gly Gly Ser Glu Arg Gly Glu Thr Gly Pro Glu Glu
    450                 455                 460
Glu Leu Gln Val Ile Gln Pro Asp Lys Ser Val Ser Val Ala Ala Gly
465                 470                 475                 480
Glu Ser Ala Ile Leu His Cys Thr Val Thr Ser Leu Ile Pro Val Gly
                485                 490                 495
Pro Ile Gln Trp Phe Arg Gly Ala Gly Pro Ala Arg Glu Leu Ile Tyr
            500                 505                 510
Asn Gln Lys Glu Gly His Phe Pro Arg Val Thr Thr Val Ser Glu Ser
        515                 520                 525
Thr Lys Arg Glu Asn Met Asp Phe Ser Ile Ser Ile Ser Asn Ile Thr
    530                 535                 540
Pro Ala Asp Ala Gly Thr Tyr Tyr Cys Val Lys Phe Arg Lys Gly Ser
545                 550                 555                 560
Pro Asp Thr Glu Phe Lys Ser Gly Ala Gly Thr Glu Leu Ser Val Arg
                565                 570                 575
Ala Lys Pro Ser
            580

<210> SEQ ID NO 4
<211> LENGTH: 654
<212> TYPE: DNA
<213> ORGANISM: Artificial Sequence
<220> FEATURE:
<223> OTHER INFORMATION: nucleotide sequence encoding light chain of
      anti-PD-1 antibody of recombinant protein

<400> SEQUENCE: 4
gacatcgtgc tgacccagtc ccctgcttcc ctggctgtgt cccctggaca gagggccacc      60
atcacatgcc gggcctccga gtccgtggac aactacggca tctccttcat gaactggttc     120
cagcagaagc ccggccagcc tcccaagctg ctgatctacg ccgcctccaa caagggcaca     180
ggcgtgcctg ccaggttttt cggttctggc tccggcaccg acttcaccct gaacatcaac     240
cctatggaag aggaagacac cgccatgtac ttctgccagc agtccaagga ggtgccttgg     300
acattcggcg gcggcaccaa gctggagatc aagcggaccg tggccgctcc aagcgtcttc     360
attttttccc cttccgacga acagctgaag agtgggacag cctcagtggt ctgtctgctg     420
aacaatttct accctagaga ggctaaggtg cagtggaaag tcgataacgc actgcagtct     480
ggcaatagtc aggagtcagt gacagaacag gacagcaagg attccactta ttctctgtct     540
agtacactga ctctgtctaa agccgactac gaaaagcaca agtgtatgc ttgtgaagtg     600 acccaccagg ggctgtccag tcccgtgacc aaatctttca atagggggcga gtgt          654
```

<210> SEQ ID NO 5
<211> LENGTH: 1740
<212> TYPE: DNA
<213> ORGANISM: Artificial Sequence
<220> FEATURE:
<223> OTHER INFORMATION: nucleotide sequence encoding polypeptide of
      recombinant protein

<400> SEQUENCE: 5

| gaggtgcagc tggtccagag cggaggcgga ctggtccagc ctggcggcag cctgaagctc | 60 |
| agctgtgccg ccagcggatt caccttctcc tcctacggaa tgtcctgggt ccggcaggct | 120 |
| cctggcaaag gactgactg gtggctacc atctccggcg aggaaggga cacctactac | 180 |
| cccgactccg tcaagggcag gttcaccatc tcccgggaca tagcaagaa caacctgtat | 240 |
| ctccagatga cagcctgcg ggctgaggac accgccctgt actactgcgc tcggcagaag | 300 |
| ggcgaagcct ggttcgccta ttggggacag ggcacactgg tgaccgtgag cgccgccagc | 360 |
| acaaaaggcc ccagcgtgtt ccccctggct ccctgttcca ggagcaccag cgagtccacc | 420 |
| gctgctctgg gctgcctggt gaaggactat ttccctgagc ccgtcaccgt cagctggaat | 480 |
| agcggcgccc tgaccagcgg agtccacaca ttccccgccg tgctgcaaag cagcggcctg | 540 |
| tactccttat cttctgtcgt gaccgtgccc tccagcagcc tgggaaccaa gacctatacc | 600 |
| tgcaacgtgg accacaagcc cagcaacacc aaggtggata gcgggtcga atccaagtac | 660 |
| ggcccccctt gtcctccttg tcccgctcct gagttcctgg gaggacccag cgtgtttctg | 720 |
| ttccctccta agcccaagga caccctgatg atcagccgga ccccgaggt cacctgtgtg | 780 |
| gtggtggacg tgtcccagga ggaccccgag gtgcagttta actggtacgt ggacggcgtg | 840 |
| gaagtgcaca atgccaagac caagcccagg gaggagcagt tcaacagcac ctaccgggtg | 900 |
| gtgtccgtgc tgaccgtgct gcaccaggac tggctgaacg gcaaggagta caagtgcaaa | 960 |
| gtgtccaaca aaggcctgcc cagctccatc gagaagacca tctccaaggc caagggccaa | 1020 |
| cctcgggagc ccaagtgta tacactgccc ccttcccagg aagagatgac caagaaccag | 1080 |
| gtcagcctca cctgtctggt gaagggcttc tatcccagcg acatcgccgt cgaatgggaa | 1140 |
| tccaacggcc agcccgagaa caattacaag accaccccc ccgtgctgga ttccgacggc | 1200 |
| tccttctttc tgtatagccg gctcaccgtg gacaagagca gtggcagga gggcaacgtg | 1260 |
| ttctcctgta gcgtcatgca cgaggccctg cacaaccact acacccagaa atccctgtcc | 1320 |
| ctgtccctgg gaaagggcgg cggcggctcc ggcggaggag gcagcgaaag gggcgaaacc | 1380 |
| ggccctgagg aggagttaca agtgatccag cccgacaagt ccgtgtccgt ggctgctggc | 1440 |
| gagtccgcta tcctgcactg caccgtgacc tccctgatcc ccgtgggccc tatccagtgg | 1500 |
| ttcagggag ctggccccgc tagggagctg atctacaacc agaaggaggg ccacttcccc | 1560 |
| agggtgacca ccgtgtccga gagcaccaag agggagaaca tggacttctc catcagcatc | 1620 |
| tccaacatca cccccgctga cgccggcacc tactactgcg tgaagttcag gaagggcagc | 1680 |
| cccgacaccg agttcaagtc cggcgctggc accgagctgt ccgtgagggc caaaccctcc | 1740 |

<210> SEQ ID NO 6
<211> LENGTH: 445
<212> TYPE: PRT
<213> ORGANISM: Artificial Sequence
<220> FEATURE:
<223> OTHER INFORMATION: amino acid sequence of heavy chain of anti-PD-1
      antibody in recombinant protein

<400> SEQUENCE: 6

-continued

```
Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Ala Pro Gly Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Arg Gln Lys Gly Glu Ala Trp Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415
```

```
Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 7
<211> LENGTH: 118
<212> TYPE: PRT
<213> ORGANISM: Artificial Sequence
<220> FEATURE:
<223> OTHER INFORMATION: amino acid sequence of human SIRPA
      extracellular segment in recombinant protein

<400> SEQUENCE: 7

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 8
<211> LENGTH: 1335
<212> TYPE: DNA
<213> ORGANISM: Artificial Sequence
<220> FEATURE:
<223> OTHER INFORMATION: nucleotide sequence encoding heavy chain of
      anti-PD-1 antibody in recombinant protein

<400> SEQUENCE: 8
gaggtgcagc tggtccagag cggaggcgga ctggtccagc ctggcggcag cctgaagctc      60
agctgtgccg ccagcggatt caccttctcc tcctacggaa tgtcctgggt ccggcaggct     120
cctggcaaag gactgactg gtggctacc atctccggcg aggaaggga cacctactac        180 cccgactccg tcaagggcag gttcaccatc tcccgggaca tagcaagaa caacctgtat     240 ctccagatga cagcctgcg ggctgaggac accgccctgt actactgcgc tcggcagaag     300
ggcgaagcct ggttcgccta tggggacag gcacactgg tgaccgtgag cgccgccagc      360
acaaaaggcc ccagcgtgtt ccccctggct cctgttcca ggagcaccag cgagtccacc    420
gctgctctgg ctgcctggt gaaggactat ttccctgagc ccgtcaccgt cagctggaat    480
agcggcgccc tgaccagcgg agtccacaca ttccccgccg tgctgcaaag cagcggcctg   540
tactccttat cttctgtcgt gaccgtgccc tccagcagcc tgggaaccaa gacctatacc    600
tgcaacgtgg accacaagcc cagcaacacc aaggtggata gcgggtcga atccaagtac    660 ggcccccctt gtcctccttg tcccgctcct gagttcctgg aggacccag cgtgtttctg     720 ttccctccta agcccaagga cacctgatg atcagccgga cccccgaggt cacctgtgtg    780
gtggtggacg tgtcccagga ggaccccgag gtgcagttta ctggtacgt ggacggcgtg   840
```

```
gaagtgcaca atgccaagac caagcccagg gaggagcagt tcaacagcac ctaccgggtg      900
gtgtccgtgc tgaccgtgct gcaccaggac tggctgaacg gcaaggagta caagtgcaaa      960
gtgtccaaca aaggcctgcc cagctccatc gagaagacca tctccaaggc caagggccaa     1020
cctcgggagc cccaagtgta tactgcccc  ccttccagg  aagagatgac caagaaccag     1080
gtcagcctca cctgtctggt gaagggcttc tatcccagcg acatcgccgt cgaatgggaa     1140
tccaacggcc agcccgagaa caattacaag accacccccc ccgtgctgga ttccgacggc     1200
tccttctttc tgtatagccg gctcaccgtg gacaagagca ggtggcagga gggcaacgtg     1260
ttctcctgta gcgtcatgca cgaggccctg cacaaccact acacccagaa atccctgtcc     1320
ctgtccctgg gaaag                                                      1335

<210> SEQ ID NO 9
<211> LENGTH: 51
<212> TYPE: DNA
<213> ORGANISM: Artificial Sequence
<220> FEATURE:
<223> OTHER INFORMATION: nucleotide sequence encoding linker in
      recombinant protein

<400> SEQUENCE: 9
ggcggcggcg gctccggcgg aggaggcagc gaaaggggcg aaaccggccc t                51

<210> SEQ ID NO 10
<211> LENGTH: 354
<212> TYPE: DNA
<213> ORGANISM: Artificial Sequence
<220> FEATURE:
<223> OTHER INFORMATION: nucleotide sequence encoding human SIRPA
      extracellular segment in recombinant protein

<400> SEQUENCE: 10
gaggaggagt tacaagtgat ccagcccgac aagtccgtgt ccgtggctgc tggcgagtcc       60
gctatcctgc actgcaccgt gacctccctg atccccgtgg gccctatcca gtggttcagg      120
ggagctggcc ccgctaggga gctgatctac aaccagaagg agggccactt ccccagggtg      180
accaccgtgt ccgagagcac caagagggag aacatggact tctccatcag catctccaac      240
atcacccccg ctgacgccgg cacctactac tgcgtgaagt tcaggaaggg cagccccgac      300
accgagttca gtccggcgc  tggcaccgag ctgtccgtga gggccaaacc ctcc            354
```

ANTI-PD-1/CD47 BISPECIFIC ANTIBODY AND APPLICATION THEREOF

CROSS-REFERENCE TO RELATED APPLICATIONS

This application is a U.S. continuation application based upon PCT Application No. PCT/CN2017/115323, filed with the China National Intellectual Property Administration on Dec. 8, 2017, the entire content of which is incorporated herein by reference.

FIELD

The present disclosure relates to the field of immunology and antibody engineering technology, in particular to a bi-specific antibody against PD-1 and CD47 and application thereof. More particularly the disclosure relates to recombinant antibodies, nucleic acids, constructs, a method for preparing recombinant antibody, a therapeutic composition for treating cancers and a method for treating cancers.

BACKGROUND

Cancer has become one of the leading causes of death worldwide in recent years. According to the World Health Organization report, the number of cancer deaths worldwide reached nearly 8.8 million in 2015, accounting for about one sixth of the total annual deaths. In 2015, there were about 4.292 million of newly diagnosed cancer cases and 2.814 million of cancer deaths in China. The cancer incidence rate is still rising in China.

At present, cancer therapy is mainly focused on surgery, radiotherapy and chemotherapy, but traditional therapies have the disadvantages of poor tumor specificity and large toxicity and side effects. Therefore, there is a strong demand on safer and more effective methods having higher specificity for treating cancers. In recent years, with the deepening understanding on cancer mechanism, molecular targeted therapies that inhibit tumor growth by using specific antibodies have gradually emerged. Under the circumstances, the antibody medicament which is prepared according to antibody engineering technology mainly based on cell engineering technology and genetic engineering technology, exhibits advantages of high specificity, remarkable therapeutic effects, low toxicity and side effects and the like, thus having very broad prospects for cancer treatment. Recently, with the discovery of immune checkpoints, specific antibodies targeting the immune checkpoints are developed to inhibit the immune escape of tumor cells, which pushes the immunotherapy to a new stage.

In the immune system, the activation of T cells is complicated, depending on not only a first stimulation signal provided by the MHC-TCR complex, but also a second stimulation signal (i.e., a co-stimulation signal) provided by molecules on the surface of antigen presenting cell. Lacking such a co-stimulation signal will lead T cells non-response, tolerance and apoptosis. Programmed death receptor-1 (PD-1, also known as CD279) and its ligands (ligands 1 and 2 of PD-1, i.e. PD-L1 and PD-L2) are such inhibiting co-stimulation molecules.

The PD-1/PD-L1 signaling pathway which plays a key role in tumor immunity has become a new molecular target in tumor immunotherapy. Inhibition of T cells (i.e. main cellular immunity cells) by tumor cells can be blocked by blocking the PD-1/PD-L1 signaling pathway. The development of anti-PD-1 antibody and anti-PD-L1 antibody has become a popular research direction in tumor immunotherapy research. Monoclonal antibodies targeting PD-1 that have been approved by the Food and Drug Administration (FDA) of USA include Keytruda (pembrolizumab) from Merck and Opdivo (Nivolumab) from Bristol-Myers Squibb. Monoclonal antibodies targeting PD-L1 include Tecentriq (Atezolizumab) from Roche, Bavencio (avelumab) produced by Pfizer and Merck, and Imfinzi (Durvalumab) from AstraZeneca. These monoclonal antibodies have already achieved good clinical results on not only melanoma and metastatic squamous non-small cell lung cancer and other tumors that have progressed after chemotherapy (i.e. cancers to which the monoclonal antibody was firstly applied), but also the newly applied Hodgkin's lymphoma, renal cancer, gastric cancer, anal carcinoma, liver cancer, colorectal cancer and the like. In addition, several anti-PD-1 and anti-PD-L1 antibodies have entered clinical trials for the treatment of tumors.

Currently, the biggest limitation of immunotherapy is low efficacy, with 15% to 50% of efficacy to PD-1. Research evidence has showed that successful cancer immunotherapy depends on whether a systemic immune response can be triggered, rather than triggering local immune response of tumor only. Generating a systemic immune response upon stimulation to immune system is expected to significantly increase the efficacy of immunotherapy.

SUMMARY

The present disclosure aims to solve one of the technical problems in the related art at least to some extent.

In one aspect, provided in the present disclosure is a recombinant antibody, i.e. a recombinant protein. In an embodiment of the present disclosure, the recombinant protein comprises a) an anti-PD-1 antibody, and b) a human signal regulatory protein α (SIRPA) extracellular segment capable of binding CD47, wherein the N-terminus of the human SIRPA extracellular segment is connected to the C-terminus of heavy chain of the anti-PD-1 antibody. Thus, the recombinant protein according to the embodiment is capable of targeting both PD-1 and CD47, thus can significantly enhance the stimulation to immune system and exhibit stronger tumor suppressing ability than the antibody against a single target.

According to this embodiment, the recombinant protein further comprises a linker, connecting the C-terminus of heavy chain of the anti-PD-1 antibody to the N-terminus of the human SIRPA extracellular segment, thereby avoiding the interaction effect of steric hindrance of proteins and further promoting the protein folding.

In another embodiment of the present disclosure, the recombinant protein comprises a) a light chain of the anti-PD-1 antibody, and b) a polypeptide comprising a heavy chain of the anti-PD-1 antibody and the human SIRPA extracellular segment capable of binding CD47. Thus, the recombinant antibody according to the embodiment is capable of targeting both PD-1 and CD47, thus can significantly enhance the stimulation to immune system and exhibit stronger tumor suppressing ability than the antibody against a single target.

According to this embodiment, the polypeptide further comprises a linker, connecting the C-terminus of heavy chain of the anti-PD-1 antibody to the N-terminus of the human SIRPA extracellular segment, thereby avoiding the interaction effect of steric hindrance of proteins and further promoting the protein folding.

In an embodiment of the present disclosure, the linker comprises the amino acid sequence of SEQ ID NO: 1.

```
SEQ ID NO: 1, the amino acid sequence of linker of
the recombinant protein
                                           (SEQ ID NO: 1)
GGGGSGGGGSERGETGP.
```

In an embodiment of the present disclosure, the anti-PD-1 antibody is an IgG-like antibody against PD-1.

Preferably, the IgG-like antibody is an IgG4 subtype. IgG4 is easily to form an incomplete antibody, with Fab-arm exchange. The S228P modification of IgG4 subtype antibody can effectively reduce Fab-arm exchange and thus effectively avoid the effects of antibody-dependent cell-mediated cytotoxicity (ADCC) and complement dependent cytotoxicity (CDC).

In an embodiment of the present disclosure, the anti-PD-1 antibody is HX008 18A10 antibody (i.e. also called as H8 antibody hereinafter), referring to the contents described in patent application Nos. 201610207741.6 and PCT/CN2016/103814.

In an embodiment of the present disclosure, provided in the present disclosure is a recombinant protein, comprising a) a light chain of the anti-PD-1 antibody comprising the amino acid sequence of SEQ ID NO: 2, and b) a polypeptide comprising the amino acid sequence of SEQ ID NO: 3. According to this embodiment, the polypeptide comprises a heavy chain of the anti-PD-1 antibody and the human SIRPA extracellular segment capable of binding CD47. According to this embodiment, the polypeptide further comprises a linker, connecting the C-terminus of heavy chain of the anti-PD-1 antibody to the N-terminus of the human SIRPA extracellular segment.

```
SEQ ID NO: 2, the amino acid sequence of light
chain of the anti-PD-1 antibody in the
recombinant protein
                                           (SEQ ID NO: 2)
DIVLTQSPASLAVSPGQRATITCRASESVDNYGISFMNWFQQKPGQPPKL

LIYAASNKGTGVPARFSGSGSGTDFTLNINPMEEEDTAMYFCQQSKEVPW

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

SEQ ID NO: 3, the amino acid sequence of the
polypeptide of the recombinant protein
                                           (SEQ ID NO: 3)
EVQLVQSGGGLVQPGGSLKLSCAASGFTFSSYGMSWVRQAPGKGLDWVAT

ISGGGRDTYYPDSVKGRFTISRDNSKNNLYLQMNSLRAEDTALYYCARQK

GEAWFAYWGQGTLVTVSAASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKGGGGS

GGGGSERGETGPEEELQVIQPDKSVSVAAGESAILHCTVTSLIPVGPIQW
```
```
-continued
FRGAGPARELIYNQKEGHFPRVTTVSESTKRENMDFSISISNITPADAGT

YYCVKFRKGSPDTEFKSGAGTELSVRAKPS.
```

According to the embodiment, it is indicated that the anti-PD-1 antibody comprises a heavy chain comprising an amino acid sequence of SEQ ID NO: 6, which is comprised in the amino acid sequence of SEQ ID NO: 3 as described above.

```
SEQ ID NO: 6, the amino acid sequence of heavy
chain of the anti-PD-1 antibody in the recombinant
protein
                                           (SEQ ID NO: 6)
EVQLVQSGGGLVQPGGSLKLSCAASGFTFSSYGMSWVRQAPGKGLDWVAT

ISGGGRDTYYPDSVKGRFTISRDNSKNNLYLQMNSLRAEDTALYYCARQK

GEAWFAYWGQGTLVTVSAASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK.
```

According to the embodiment, it is indicated that the human SIRPA extracellular segment of the recombinant protein comprises an amino acid sequence of SEQ ID NO: 7, which is comprised in the amino acid sequence of SEQ ID NO: 3 as described above.

```
SEQ ID NO: 7, the amino acid sequence of the human
SIRPA extracellular segment in the recombinant
protein
                                           (SEQ ID NO: 7)
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPS.
```

The recombinant protein according to the embodiment is capable of targeting both PD-1 and CD47, thus can significantly enhance the stimulation to immune system and exhibit stronger tumor suppressing ability than the antibody against a single target.

In another aspect, provided in the present disclosure is a nucleic acid. In an embodiment of the present disclosure, the nucleic acid encodes the recombinant antibody as described above. The recombinant antibody encoded by the nucleic acid according to the embodiment is capable of targeting both PD-1 and CD47, thus can significantly enhance the stimulation to immune system and exhibit stronger tumor suppressing ability than the antibody against a single target.

In an embodiment of the present disclosure, the nucleic acid comprises a first nucleotide sequence encoding the light chain of the anti-PD-1 antibody, when combined with the polypeptide, forms an antigen-binding site that binds PD-1; and a second nucleotide sequence encoding the polypeptide.

In an embodiment of the present disclosure, the first nucleotide sequences comprises the nucleotide sequence of SEQ ID NO: 4, encoding the light chain of the anti-PD-1 antibody of SEQ ID NO: 2 as described above; and the second nucleotide sequences comprises the nucleotide sequence of SEQ ID NO: 5, encoding the polypeptide of SEQ ID NO: 3. According to this embodiment, the polypeptide comprises a heavy chain of the anti-PD-1 antibody and the human SIRPA extracellular segment capable of binding CD47. According to this embodiment, the polypeptide further comprises a linker, connecting the C-terminus of heavy chain of the anti-PD-1 antibody to the N-terminus of the human SIRPA extracellular segment.

SEQ ID NO: 4, the nucleotide sequence encoding the light chain of the anti-PD-1 antibody in the recombinant protein
(SEQ ID NO: 4)
gacatcgtgctgacccagtccctgcttccctggctgtgtccctggaca gagggccaccatcacatgccgggcctccgagtccgtggacaactacgca tctccttcatgaactggttccagcagaagcccggccagcctcccaagctg ctgatctacgccgcctccaacaagggcacaggcgtgcctgccaggttttc cggttctggctccggcaccgacttcaccctgaacatcaaccctatggaag aggaagacaccgccatgtacttctgccagcagtccaaggaggtgccttgg acattcggcggcggcaccaagctggagatcaagcggaccgtggccgctcc aagcgtcttcattttccccttccgacgaacagctgaagagtgggacag cctcagtggtctgtctgctgaacaatttctaccctagagaggctaaggtg cagtggaaagtcgataacgcactgcagtctggcaatagtcaggagtcagt gacagaacaggacagcaaggattccacttattctctgtctagtacactga ctctgtctaaagccgactacgaaaagcacaaagtgtatgcttgtgaagtg acccaccaggggctgtccagtcccgtgaccaaatctttcaatagggggcga gtgt.

SEQ ID NO: 5, the nucleotide sequence encoding the polypeptide of the recombinant protein
(SEQ ID NO: 5)
gaggtgcagctggtccagagcggaggcggactggtccagcctggcggcag cctgaagctcagctgtgccgccagcggattcaccttctcctcctacggaa tgtcctgggtccggcaggctcctggcaaaggactggactgggtggctacc atctccggcggaggaagggacacctactaccccgactccgtcaagggcag gttcaccatctcccgggacaatagcaagaacaacctgtatctccagatga acagcctgcgggctgaggacaccgccctgtactactgcgctcggcagaag ggcgaagcctggttcgcctattggggacagggcacactggtgaccgtgag cgccgccagcacaaaaggcccagcgtgttccccctggctccctgttcca ggagcaccagcgagtccaccgctgctctgggctgcctggtgaaggactat ttccctgagcccgtcaccgtcagctggaatagcggcgccctgaccagcgg agtccacacattccccgccgtgctgcaaagcagcggcctgtactccttat cttctgtcgtgaccgtgccctccagcagcctgggaaccaagacctatacc tgcaacgtggaccacaagcccagcaacaccaaggtggataagcgggtcga atccaagtacggcccccccttgtcctccttgtcccgctcctgagttcctgg gaggacccagcgtgtttctgttccctcctaagcccaaggacaccctgatg atcagccggaccccgaggtcacctgtgtggtggtggacgtgtcccagga ggaccccgaggtgcagtttaactggtacgtggacggcgtggaagtgcaca atgccaagaccaagcccagggaggagcagttcaacagcacctaccgggtg gtgtccgtgctgaccgtgctgcaccaggactggctgaacggcaaggagta caagtgcaaagtgtccaacaaaggcctgcccagctccatcgagaagacca tctccaaggccaagggccaacctcgggagccccaagtgtatacactgccc ccttcccaggaagagatgaccaagaaccaggtcagcctcacctgtctggt gaagggcttctatcccagcgacatcgccgtcgaatgggaatccaacggcc agcccgagaacaattacaagaccacccccccgtgctggattccgacggc tccttctttctgtatagccggctcaccgtggacaagagcaggtggcagga gggcaacgtgttctcctgtagcgtcatgcacgaggccctgcacaaccact acacccagaaatccctgtccctgtccctgggaaagggcggcggcggctcc ggcggaggaggcagcgaaaggggcgaaaccggccctgaggaggagttaca agtgatccagcccgacaagtccgtgtccgtggctgctggcgagtccgcta tcctgcactgcaccgtgacctccctgatccccgtgggccctatccagtgg ttcaggggagctggccccgctagggagctgatctacaaccagaaggaggg ccacttccccagggtgaccaccgtgtccgagagcaccaagagggagaaca tggacttctccatcagcatctccaacatcaccccgctgacgccggcacc tactactgcgtgaagttcaggaagggcagccccgacaccgagttcaagtc cggcgctggcaccgagctgtccgtgagggccaaaccctcc.

According to this embodiment, it is indicated that the heavy chain of the anti-PD-1 antibody comprising the amino acid sequence of SEQ ID NO: 6 as described above is encoded by the nucleotide sequence of SEQ ID NO: 8, which is comprised in the nucleotide sequence of SEQ ID NO: 5 as described above.

SEQ ID NO: 8, the nucleotide sequence encoding the heavy chain of the anti-PD-1 antibody in the recombinant protein
(SEQ ID NO: 8)
gaggtgcagctggtccagagcggaggcggactggtccagcctggcggcag cctgaagctcagctgtgccgccagcggattcaccttctcctcctacggaa tgtcctgggtccggcaggctcctggcaaaggactggactgggtggctacc atctccggcggaggaagggacacctactaccccgactccgtcaagggcag gttcaccatctcccgggacaatagcaagaacaacctgtatctccagatga acagcctgcgggctgaggacaccgccctgtactactgcgctcggcagaag ggcgaagcctggttcgcctattggggacagggcacactggtgaccgtgag cgccgccagcacaaaaggcccagcgtgttccccctggctccctgttcca ggagcaccagcgagtccaccgctgctctgggctgcctggtgaaggactat ttccctgagcccgtcaccgtcagctggaatagcggcgccctgaccagcgg agtccacacattccccgccgtgctgcaaagcagcggcctgtactccttat cttctgtcgtgaccgtgccctccagcagcctgggaaccaagacctatacc tgcaacgtggaccacaagcccagcaacaccaaggtggataagcgggtcga atccaagtacggcccccccttgtcctccttgtcccgctcctgagttcctgg gaggacccagcgtgtttctgttccctcctaagcccaaggacaccctgatg atcagccggaccccgaggtcacctgtgtggtggtggacgtgtcccagga ggaccccgaggtgcagtttaactggtacgtggacggcgtggaagtgcaca -continued

```
atgccaagaccaagcccagggaggagcagttcaacagcacctaccgggtg gtgtccgtgctgaccgtgctgcaccaggactggctgaacggcaaggagta caagtgcaaagtgtccaacaaaggcctgcccagctccatcgagaagacca tctccaaggccaagggccaacctcgggagccccaagtgtatacactgccc ccttcccaggaagagatgaccaagaaccaggtcagcctcacctgtctggt gaagggcttctatcccagcgacatcgccgtcgaatgggaatccaacggcc agcccgagaacaattacaagaccaccccccccgtgctggattccgacggc tccttctttctgtatagccggctcaccgtggacaagagcaggtggcagga gggcaacgtgttctcctgtagcgtcatgcacgaggccctgcacaaccact acacccagaaatccctgtccctgtccctgggaaag.
```

According to this embodiment, it is indicated that the linker comprising the amino acid sequence of SEQ ID NO: 1 as described above is encoded by the nucleotide sequence of SEQ ID NO: 9, which is comprised in the nucleotide sequence of SEQ ID NO: 5 as described above.

```
SEQ ID NO: 9, the nucleotide sequence encoding the
linker in the recombinant protein
                                    (SEQ ID NO: 9)
ggcggcggcggctccggcggaggaggcagcgaaaggggcgaaaccggccc
t.
```

According to this embodiment, it is indicated that the human SIRPA extracellular segment comprising the amino acid sequence of SEQ ID NO: 7 as described above is encoded by the nucleotide sequence of SEQ ID NO: 10, which is comprised in the nucleotide sequence of SEQ ID NO: 5 as described above.

```
SEQ ID NO: 10, the nucleotide sequence encoding
the human SIRPA extracellular segment of the
recombinant protein
                                    (SEQ ID NO: 10)
gaggaggagttacaagtgatccagcccgacaagtccgtgtccgtggctgc tggcgagtccgctatcctgcactgcaccgtgacctccctgatccccgtgg gccctatccagtggttcaggggagctggccccgctagggagctgatctac aaccagaaggagggccacttccccagggtgaccaccgtgtccgagagcac caagagggagaacatggacttctccatcagcatctccaacatcacccccg ctgacgccggcacctactactgcgtgaagttcaggaagggcagcccgac accgagttcaagtccggcgctggcaccgagctgtccgtgagggccaaacc ctcc.
```

The recombinant protein encoded by the nucleic acid according to the embodiment is capable of targeting both PD-1 and CD47, thus can significantly enhance the stimulation to immune system and exhibit stronger tumor suppressing ability than the antibody against a single target.

In another aspect, provided in the present disclosure is a construct. In an embodiment of the present disclosure, the construct comprises a first nucleic acid molecule encoding the light chain of the anti-PD-1 antibody, and a second nucleic acid molecule encoding the polypeptide as described above. According to the embodiment, the polypeptide comprises a) a light chain of the anti-PD-1 antibody, and b) a heavy chain of the anti-PD-1 antibody and the human SIRPA extracellular segment capable of binding CD47. According to the embodiment, the polypeptide further comprises a linker, connecting the C-terminus of heavy chain of the anti-PD-1 antibody to the N-terminus of the human SIRPA extracellular segment. After the construct in the embodiment is introduced into recipient cells, the expressed recombinant protein is capable of targeting both PD-1 and CD47, thus can significantly enhance the stimulation to immune system and exhibit stronger tumor suppressing ability than the antibody against a single target.

In an embodiment of the present disclosure, the construct further comprises a promoter, operably linked to the first nucleic acid molecule. The promoter can effectively initiate the expression of the first nucleic acid molecule and the second nucleic acid molecule, thereby achieving the expression of the recombinant antibody as described above.

In an embodiment of the present disclosure, the promoter is selected from U6, H1, CMV, EF-1, LTR or RSV promoters. The present inventors have found that the U6, H1, CMV, EF-1, LTR or RSV promoters can effectively initiate the expression of the first nucleic acid molecule and the second nucleic acid molecule, and also significantly improving the expression efficiency of the first and second nucleic acid molecules.

In an embodiment of the present disclosure, the vector of the construct is a non-pathogenic viral vector. The pathogenic site of the vector of the construct in the embodiment has been modified or mutated, thus the vector is non-pathogenic virus. Therefore, the treatment mediated by the non-pathogenic viral vector according to the embodiment is of a high safety.

In an embodiment of the present disclosure, the viral vector comprises at least one selected from a retroviral vector, a lentiviral vector or an adenovirus-related viral vector. The vector as described above can realize highly effective expression of the carried nucleic acid in recipient cells, with high treatment efficiency.

In another aspect, provided in the present disclosure is a method for preparing the recombinant protein as described above. In an embodiment of the present disclosure, the method comprises introducing the construct into a mammalian cell, and culturing the mammalian cell under a condition suitable for protein expression and secretion to obtain the recombinant antibody. The method according to the embodiment can obtain the recombinant antibody as described above in a simply and efficient manner. As described above, the recombinant antibody is capable of targeting both PD-1 and CD47, thus can significantly enhance the stimulation to immune system and exhibit stronger tumor suppressing ability than the antibody against a single target.

In an embodiment of the present disclosure, the mammalian cell comprises at least one selected from CHOK1, CHOS, 293F and 293T.

In another aspect, provided in the present disclosure is a therapeutic composition for treating cancers. In an embodiment of the present disclosure, the therapeutic composition comprises the construct, the recombinant antibody or the nucleic acid as described above. The therapeutic composition according to the embodiment exhibits significantly increased therapeutic effect on cancers.

In embodiments of the present disclosure, the therapeutic composition to be administered to a patient is preferably applied in a biocompatible solution or a pharmaceutically acceptable carrier. Various prepared therapeutic compositions may be suspended or dissolved in a pharmaceutically or physiologically acceptable carrier, such as physiological saline, isotonic saline or other formulations obvious for skilled in the art. The appropriate carrier depends on the administration route to a large extent. Other aqueous or non-aqueous isotonic sterile injections and aqueous or non-aqueous sterile suspensions are pharmaceutically acceptable carriers.

In another aspect, provided in the present disclosure is a method for treating cancers. In an embodiment of the present disclosure, the method comprises administering the construct, the recombinant antibody or the nucleic acid as described above to a patient suffered from cancer. The method according to the embodiment exhibits significantly increased therapeutic effect on cancers.

Additional aspects and advantages of the present disclosure will be partially given in the following description, and some will become apparent from the following description, or be learned through the practice of the present disclosure.

DETAILED DESCRIPTION

Figure 1:
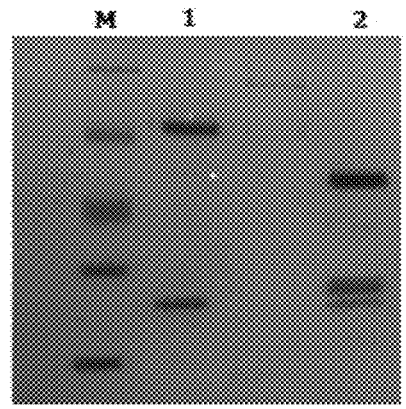
FIG. 1 is a result showing identification of HX009-5 by SDS-PAGE according to an embodiment of the present disclosure.

One object of the present disclosure is to provide a new and bi-specific antibody capable of targeting both PD1 and CD47.

Human PD-1 belongs to type I transmembrane glycoprotein of the CD28 family, with about 55 kDa of molecular weight. The human PD-1 contains two tyrosine residues (i.e., Y223 and Y248) in the intracellular domain, respectively involving in formation of an N-terminal immunoreceptor tyrosine-based inhibitory motif (ITIM, motif VDYGEL) and a C-terminal immunoreceptor tyrosine-based switch motif (ITSM, motif TEYATI). The ITIM motif can recruit intracellular SHP-2 and make downstream proteins phosphorylated, reduce BCR or TCR receptor signaling and ultimately inhibit proliferation of lymphocyte, production of cytokine and induce arrest of cell division cycle. The human PD-1 has an IgV-like domain in the extracellular region. Such an IgV-like domain contains multiple glycosylation sites and is heavily glycosylated, which is mainly involved in binding with ligands and exerts the function of inhibiting T cell activation. Unlike other co-stimulation molecules that exist in dimeric form, the PD-1 can exist as a monomer for the extracellular region of PD-1 lacks cysteine residues. PD-1 is expressed in activated T cells and B cells, as well as in monocytes, dendritic cells (DCs) and T regulatory cells (Tregs).

The two ligands of PD-1, (i.e. PD-L1, B7-H1, also known as CD274, and PD-L2, B7-DC), are type I glycoproteins belonging to members of the B7 protein family. The main ligand of PD-1, PD-L1, contains an IgV-like region, an IgC-like region, a transmembrane region and a cytoplasmic region, in which the cytoplasmic region participates in intracellular signal transduction, and the IgV-like region and IgC-like region participate in intercellular signal transduction. The PD-1 expression is positively regulated by some inflammatory factors, such as interleukin 4 (IL-4), tumor necrosis factor alpha (TNF-α) and interferon gamma (IFN-γ). In addition to expression in activated T cells, B cells, macrophages, dendritic cells and various tumor cells, PD-L1 is also widely expressed in nonlymphoid organs such as heart, blood vessel, placenta, skeletal muscle, lung, liver, spleen, thymus and the like. PD-L2 is expressed mainly in activated macrophages, DCs and a few tumor cells.

The immune suppressive effect of PD-1/PD-L1 signaling pathway plays an important role in the occurrence and development of various immune disorders, for example, autoimmune diseases. Mice lacking PD-1 would exhibit delayed and organ-specific autoimmunity. The absence of PD-1 showed accelerated tissue-specific autoimmune characterization in a lupus erythematosus LPR mouse model and a diabetes NOD mouse model involving autoimmune diseases. In addition, functionality-defective cytotoxic lymphocyte cells (CTL) that overexpress PD-1 are found in chronic infectors with such as viruses HIV, HBV and the like, while blocking PD-1 signal can reverse the functionality of CTLs and clear viruses.

Tumor cells perform immune escape by immune suppression of PD-1/PD-L1 signaling pathway. Various tumor cells can up-regulate the expression of PD-L1, such as non-small cell lung cancer (NSCLC), melanoma, lymphoma, breast cancer, leukemia and various urinary tract tumors, digestive tract tumors, reproductive system tumors and the like. Overexpressed PD-L1 interacts with the PD-1 receptor on the surface of T cells, so that the tyrosine in the ITSM domain of PD-1 is phosphorylated, which in turn causes dephosphorylation of downstream phosphatidylinositol 3-kinase (PI3K) and tyrosine kinase (Syk), thus inhibiting the activation of downstream AKT, ERK and other pathways, ultimately inhibiting the transcription and translation of genes and cytokines needed for T cell activation. On the other hand, studies have shown that PD-L1 causes accumulation of PD-1 in T cells, leading to cell cycle arrest and large accumulation of cells in G0/G1 phase. It is also found by in vitro experiments and mouse models that activation of PD-1/PD-L1 signaling pathway may lead to apoptosis of specific CTLs, thus reducing the sensitivity of cytotoxic killing effect of CTLs and promoting immune escape of tumor cells. In summary, tumor cells can inhibit the activation, proliferation and tumor killing ability of T cells by expressing PD-L1 which interacts with PD-1 on surface of T cells.

CD47, also known as integrin associated protein (IAP), is a transmembrane glycoprotein with a molecular weight of about 50 kDa, belonging to the immunoglobulin (Ig) superfamily. The CD47 comprises an N-terminal extracellular IgV domain, five highly hydrophobic transmembrane segments and a C-terminal cytoplasmic region, which can interact with signal regulatory protein α (SIRPα), thrombospondin-1 (TSP1) and integrins, and participate in regulation of transmembrane migration and phagocytosis of immune cells such as T cells, monocytes and the like.

CD47 ligand, i.e. SIRPα protein, also known as CD172a or SH2 domain-containing protein tyrosine phosphatase substrate-1 (SHPS-1), is a transmembrane glycoprotein, belonging to the immunoglobulin superfamily, where the N-terminus of SIRPα protein is bound to CD47. The SIRPα protein is expressed widely in dendritic cells (DCs), macrophages, mast cells, granulocytes, nerve cells and hematopoietic stem cells, but expressed less in other cells. The binding of SIRPα protein to CD47 results in phosphorylation of the immunoreceptor tyrosine inhibitory motif (ITIM) in the C-terminal cytoplasmic region, thereby incurring recruitment and phosphorylation of tyrosine phosphatases SHP-1 and SHP-2, and activating downstream signaling pathways, thus inhibiting phagocytosis of macrophages.

CD47 is widely expressed on the surface of various types of cells, releasing a "don't eat me" signal. CD47 is an important self-labeling protein on the cell surface and releases an important signal for regulating phagocytosis of macrophages. CD47 can bind to SIRPα protein on the surface of macrophages, and cause phosphorylation of the ITIM, and then recruitment of SHP-1 protein to produce a series of cascade reactions, thus inhibiting phagocytosis of macrophages. CD47 is highly expressed in active red blood cells and lowly expressed in senescent red blood cells, allowing specific attack and clearance of senescent red blood cells by macrophages. It is found that tumor cells can use CD47 (releasing "don't eat me" signal) to escape the attack of body's immune system. Different studies showed that CD47 has been firstly identified as a tumor antigen of human ovarian cancer in the 1980s, subsequently CD47 was also found to be expressed in a variety of human tumor types including acute myeloid leukemia (AML), chronic myeloid leukemia (CML), acute lymphoblastic leukemia (ALL), non-Hodgkin's lymphoma (NHL), multiple myeloma (MM) and other solid tumors in an expression level significantly higher than normal cells. Therefore, the signaling pathway of CD47 and its ligand SIRPα protein has become a new target for inhibiting the immune escape of tumor cells. In recent years, medicine development based on this signaling pathway has received continuous attention.

There are various mechanisms for blocking the binding of CD47 to SIRPα protein through drugs to suppress the immune escape of tumors. First, physically blocking the binding of CD47 to SIRPα protein can relieve the suppression of SIRPα protein on macrophages, which does not depend on the cytotoxic effect mediated by Fc fragment of antibody, belonging to non-innate immunity. It has been discovered that anti-CD47 antibody lacking Fc fragment can still promote the clearance of tumors by macrophages. Second, blocking CD47 can directly induce apoptosis of tumors, without relying on macrophages. Third, anti-CD47 antibody can induce antigen presentation and initiate anti-tumor adaptive immunity through activation of T cells and DC cells both expressing SIRPα. Blocking the signaling pathways between CD47 and SIRPα can relieve the inhibition of DC maturation and cytokine production. DC cells are capable of killing tumor cells via the synergistic effect of CD47 antibody and phagocytes, and present tumor-associated antigens to CD8+ T cells, thereby exerting the specific killing effect of CD8+ T cells on tumors.

Therefore, CD47/SIRPα antibody is an important next-generation tumor immunosuppressant product after the PD1/PD-L1 antibody. CD47 and PD-L1 have similarities, for example, both of them are regulated by the transcription factor myc and are widely expressed in various tumor cells. In some aspects, CD47 antibody may be more promising than anti-PD1/PD-L1 antibody. Specifically, CD47 is expressed more widely than PD-L1, and is highly expressed in almost all tumor cells, indicating a broader spectrum of efficacy. Further, the CD47 antibody exerts tumor suppression via more diverse mechanisms than PD-1 antibody. For example, that antibodies against traditional immunosuppressive agents such as PD-1, CTLA-4 and the like would not tumor-specifically kill T cells may be an important reason for a limited functionality such as only exhibiting effect on a small part of tissues; while the CD47 antibody can not only initiate the non-adaptive immunity mediated by macrophages, but also initiate the specific killing of tumor cells through the antigen presenting of macrophages, DC cells and the like. However, CD47 also involves the regulation of non-immune signals in different tissues due to its extensive expression, thus blocking the CD47 signal may cause macrophages attack the own normal tissues extensively, or result in some non-immune regulatory disorders. Phagocytosis by macrophages requires a synergistic effect of the "don't eat me" signal expressed by such as CD47 and the "eat me" signal expressed by such as calreticulin (CRT). Generally, tumor cells highly express CRT, but normal cells do not express CRT and the "eat me" signal, thus the CD47 antibody displays a limited blocking effect in normal tissues even through CD47 is also widely present in human cerebral cortex, cerebellum and other healthy tissues. However, according to the clinical data of the Phase I clinical trial, patients received radiotherapy and chemotherapy will express up-regulated "eat me" signal. After the CD47 antibody treatment, CD47+ red blood cells may be depleted, causing transient anemia as a main adverse reaction.

CD47 antibody therapy exerts tumor killing effects through DC cells and CD8+ T cells. DC cells are capable of killing tumor cells via the synergistic effect of CD47 antibody and phagocytes, and present tumor-associated antigens to CD8+ T cells, thereby exerting the specific killing effect of CD8+ T cells on tumors. Tumor cells up-regulate the expression of CD47 to deceive macrophages, however, the CD47 antibody can block the "don't eat me" signal expressed by CD47 to exert phagocytosis by macrophages. The recombinant antibody of the present disclosure is capable of targeting both PD-1 and CD47, thus can significantly enhance the stimulation to immune system and exhibit stronger tumor suppressing ability, which is served as a next-generation immune checkpoint inhibitor.

EXAMPLES

The examples of the present disclosure are described in detail below.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang PT), Molecular Cloning: A Laboratory Manual, 3rd Ed., Science Press) or in accordance with the product instructions. If the manufacturers of reagents or instruments are not specified, the reagents or instruments may be commercially available, for example, from Illumina Company.

The cell lines and general experimental techniques used in the following examples are described as follows.

Example 1 Protein Expression of PD-1/CD47 Bi-Specific Antibody

Based on the humanized antibody H8 (anti-PD-1 IgG antibody), a bi-specific antibody HX009-5 was obtained by linking the human signal regulatory protein alpha (SIRPA, NP_542970.1) extra-membrane domain (31aa-148aa) to the C-terminus of the H8 heavy chain via a particular linker (GGGGSGGGGSERGETGP), such that the bi-specific antibody targets both proteins PD-1 and CD47 of interest.

In practical operation, an entire sequence of a nucleic acid encoding the light chain of the humanized antibody H8 was synthesized, and then inserted into a vector, thereby obtaining an expression vector 1; also synthesized were an entire sequence of a nucleic acid encoding the H8 heavy chain and an entire sequence of a nucleic acid encoding the Linker-SIRPA (118 mer), in which the nucleic acid encoding the H8 heavy chain was directly inserted into the expression vector 1, thus obtaining an expression vector 2 expressing the anti-PD1 monoclonal antibody H8. After fusion by Over-lap PCR, the nucleic acid encoding a fusion peptide of the heavy chain of anti-PD1 monoclonal antibody H8 and Linker-SIRPA was inserted into the expression vector 1, such that an expression vector 3 expressing the bi-specific antibody HX009-5 was obtained. Afterwards, DNAs extracted from the expression vectors 2 and 3 were transfected into mammalian cells (293 cells), respectively. With such a transfection, the antibodies were expressed in the mammalian cells and secreted out of the cells. The proteins H8 and HX009-5 were then obtained after purification on the Antibody A affinity chromatography column. The HX009-5 was used for subsequent pharmacodynamics study after quality identification by SDS-PAGE and SEC-HPLC standard analysis techniques.

Figure 2:
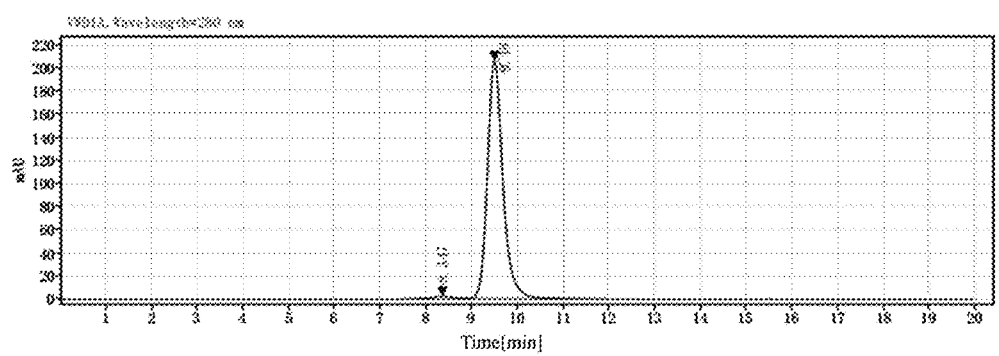
FIG. 2 is a result showing identification of HX009-5 by SEC-HPLC according to an embodiment of the present disclosure.

FIGS. 1 and 2 are results showing identification of HX009-5 by SDS-PAGE and SEC-HPLC respectively.

FIG. 1 is an SDS-PAGE result for identification of HX009-5. In FIG. 1, the lane 1 represents HX009-5 (reduced); the lane 2 represents H8 (reduced); the lane M represents a protein marker (18.4 KDa; 25 KDa; 35 KDa; 45 KDa; 66.2 KDa). As shown in FIG. 1, the candidate sample of the antibody HX009-5 exhibits relative high overall purity.

FIG. 2 is an SEC-HPLC result for identification of HX009-5. As shown in FIG. 2, the antibody is confirmed by integral quantification to have an overall purity of 98.2%.

Amino acid sequence of heavy chain of HX009-5
(SEQ ID NO: 3)
evqlvqsgqqlvqpqqslklscaasgftfssyqmswvrqapqkqldwvat isgggrdtyypdsvkgrftisrdnsknnlylqmnslraedtalyycargk geawfaywgqgtlvtvsaastkgpsvfplapcsrstsestaalgclvkdy fpepvtvswnsgaltsgvhtfpavlqssglyslssvvtvpssslgtktyt cnvdhkpsntkvdkrveskygppcppcpapeflggpsvflfppkpkdtlm isrtpevtcvvvdvsqedpevqfnwyvdgvevhnaktkpreeqfnstyrv vsvltvlhqdwlngkeykckvsnkglpssiektiskakgqprepqvytlp psqeemtknqvsltclvkgfypsdiavewesngqpennykttppvldsdg sfflysrltvdksrwqegnvfscsvmhealhnhytqkslslslgkgggqs ggggsergetgpeeelqviqpdksysvaagesailhctvtslipvgpiqw frgagpareliynqkeghfprvttvsestkrenmdfsisisnitpadagt yycvkfrkgspdtefksgagtelsvrakps, with the variable region underlined.

Nucleic acid sequence encoding heavy chain of HX009-5
(SEQ ID NO: 5)
gaggtgcagctggtccagagcggaggcggactggtccagcctggcggcag cctgaagctcagctgtgccgccagcggattcaccttctcctcctacggaa tgtcctgggtccggcaggctcctggcaaaggactggactgggtggctacc atctccggcggaggaagggacacctactaccccgactccgtcaagggcag gttcaccatctcccgggacaatagcaagaacaacctgtatctccagatga acagcctgcgggctgaggacaccgccctgtactactgcgctcggcagaag ggcgaagcctggttcgcctattggggacagggcacactggtgaccgtgag cgccgccagcacaaaaggccccagcgtgttcccctggctcctgttcca ggagcaccagcgagtccaccgctgctctgggctgcctggtgaaggactat ttccctgagcccgtcaccgtcagctggaatagcggcgccctgaccagcgg agtccacacattccccgccgtgctgcaaagcagcggcctgtactccttat cttctgtcgtgaccgtgccctccagcagcctgggaaccaagacctatacc tgcaacgtggaccacaagcccagcaacaccaaggtggataagcgggtcga atccaagtacggccccccttgtcctccttgtcccgctcctgagttcctgg gaggacccagcgtgtttctgttccctcctaagcccaaggacaccctgatg atcagccggaccccgaggtcacctgtgtggtggtggacgtgtcccagga ggaccccgaggtgcagtttaactggtacgtggacggcgtggaagtgcaca atgccaagaccaagcccagggaggagcagttcaacagcacctaccgggtg gtgtccgtgctgaccgtgctgcaccaggactggctgaacggcaaggagta caagtgcaaagtgtccaacaaaggcctgcccagctccatcgagaagacca tctccaaggccaagggccaacctcgggagccccaagtgtatacactgccc ccttcccaggaagagatgaccaagaaccaggtcagcctcacctgtctggt gaagggcttctatcccagcgacatcgccgtcgaatgggaatccaacggcc agccccgagaacaattacaagaccacccccccgtgctggattccgacggc -continued

```
tccttctttctgtatagccggctcaccgtggacaagagcaggtggcagga gggcaacgtgttctcctgtagcgtcatgcacgaggccctgcacaaccact acacccagaaatccctgtccctgtccctgggaaagggcggcggcggctcc ggcggaggaggcagcgaaaggggcgaaaccggccctgaggaggagttaca agtgatccagcccgacaagtccgtgtccgtggctgctggcgagtccgcta tcctgcactgcaccgtgacctccctgatcccgtgggccctatccagtgg ttcaggggagctggcccgctagggagctgatctacaaccagaaggaggg ccacttccccagggtgaccaccgtgtccgagagcaccaagagggagaaca tggacttctccatcagcatctccaacatcaccccgctgacgccggcacc tactactgcgtgaagttcaggaagggcagccccgacaccgagttcaagtc cggcgctggcaccgagctgtccgtgagggccaaaccctcc
```

Amino acid sequence of light chain of HX009-5
(SEQ ID NO: 2)

```
divltqspaslavspqqratitcrasesvdnyqisfmnwfqqkpqqppkl liyaasnkgtgvparfsgsgsgtdftlninpmeeedtamyfcqqskevpw tfgggtkleikrtvaapsvfifppsdeqlksgtasvvcllnnfypreakv qwkvdnalqsgnsqesvteqdskdstyslsstltlskadyekhkvyacev thqglsspvtksfnrgec,
``` with the variable region underlined.

Nucleic acid sequence encoding light chain of HX009-5
(SEQ ID NO: 4)

```
gacatcgtgctgacccagtccctgcttccctggctgtgtccctggaca gagggccaccatcacatgccgggcctccgagtccgtggacaactacggca tctccttcatgaactggttccagcagaagcccggccagcctcccaagctg ctgatctacgccgcctccaacaagggcacaggcgtgcctgccaggttttc cggttctggctccggcaccgacttcaccctgaacatcaaccctatggaag aggaagacaccgccatgtacttctgccagcagtccaaggaggtgccttgg acattcggcggcggcaccaagctggagatcaagcggaccgtggccgctcc aagcgtcttcatttttccccttccgacgaacagctgaagagtgggacag cctcagtggtctgtctgctgaacaatttctaccctagagaggctaaggtg cagtggaaagtcgataacgcactgcagtctggcaatagtcaggagtcagt gacagaacaggacagcaaggattccacttattctctgtctagtacactga ctctgtctaaagccgactacgaaaagcacaaagtgtatgcttgtgaagtg acccaccaggggctgtccagtcccgtgaccaaatctttcaatagggcga gtgt
```

Example 2 ELISA Binding Assay of HX009-5 Bi-Specific Antibody

1. PD-1 Binding ELISA Assay of H8 and HX009-5

The head-to-head comparison was conducted between the H8 antibody and the HX009-5 antibody obtained in Example 1, including the PD-1 binding assay and the PD-L1 competitive assay. Details are shown as below.

Specific steps for the PD-1 binding assay are as below.

1) Antigen Coating

An ELISA plate was coated with hPD-1-his antigen at a concentration of 0.25 μg/ml (100 μl per well) by incubation at 4° C. overnight.

2) Blocking:

The ELISA plate coated with the hPD-1-his antigen was blocked with 1% BSA (diluted in the PBS buffer) at 37° C. for 2 hours, and then washed with 1×PBST buffer containing 1% Tween-20 for three times, with gently patting to dryness.

3) Incubation with Primary Antibody

The H8 and HX009-5 antibodies each were diluted from 2 μg/ml by 1:5 in series, with 7 gradient antibody solutions obtained for each antibody. The 7 gradient antibody solutions for each antibody and the blank PBS control were respectively added into the blocked ELISA plate for incubation at 37° C. for 1 hour.

4) Incubation with Secondary Antibody

After the ELISA plate was washed with the PBST buffer for three times and gently patted to dryness, goat anti-human IgG-HRP (H+L) as a secondary antibody in 1:10000 dilution (100 μl per well) was added for incubation at 37° C. for 1 hour.

5) Developing

After the ELISA plate was washed with the PBST buffer for three times and gently patted to dryness again, 3,3',5,5'-Tetramethylbenzidine (TMB) as a developer in 100 μl per well was added for incubation at room temperature for 5 to 15 minutes.

6) Termination of Developing

2M $H_2SO_4$ solution in 50 μl per well was added to terminate developing.

7) Reading

The absorbance of solution in each well was measured on a microplate reader under a wavelength of 450 nm.

Figure 3:
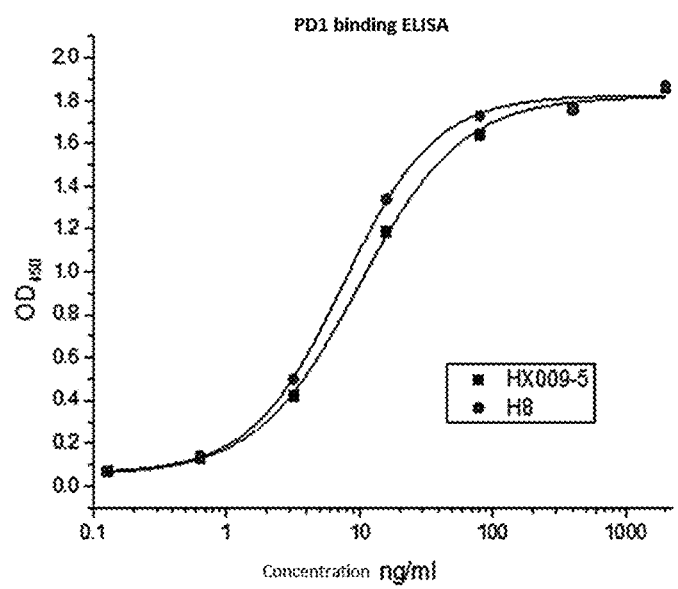
FIG. 3 is a diagram showing experimental results on affinities of H8 and HX009-5 to PD-1 according to an embodiment of the present disclosure.

As shown in Table 1 and FIG. 3, it can be calculated that the $EC_{50}$ values of H8 and HX009-5 binding to PD-1 are both 0.05 nM. FIG. 3 indicates that fusion with Linker-SIRPA (118 mer) at the C-terminus of H8 does not provide the antibody HX009-5 with any change in binding affinity to PD-1.

TABLE 1

| Dilution of antibody | H8 | | HX009-5 | |
| --- | --- | --- | --- | --- |
| 2 μg/ml | 1.881 | 1.84 | 1.9 | 1.847 |
| 1:5 | 1.756 | 1.756 | 1.784 | 1.757 |
| 1:25 | 1.661 | 1.628 | 1.716 | 1.736 |
| 1:125 | 1.214 | 1.156 | 1.341 | 1.34 |
| 1:625 | 0.429 | 0.419 | 0.514 | 0.491 |
| 1:3125 | 0.127 | 0.125 | 0.146 | 0.14 |
| 1:15625 | 0.072 | 0.066 | 0.068 | 0.069 |
| 0 | 0.052 | 0.05 | 0.054 | 0.048 |

2. PD-L1 Competitive ELISA Assay of H8 and HX009-5

Specific steps are as below.

1) Antigen Coating

A 96-well ELISA plate was coated with hPD-1-hIgGFc antigen at a concentration of 0.5 μg/ml (50 μl per well) by incubation at 4° C. overnight.

2) Blocking

After washed with the PBST buffer for three times and gently patted to dryness, the coated 96-well ELISA plate was blocked with 1% BSA (diluted in the PBS buffer) at 37° C. for 2 hours, and then washed with 1×PBST buffer containing 1% Tween-20 for three times.

3) Incubation with Primary Antibody

The H8 and HX009-5 antibodies each were diluted from 6 μg/ml by 1:3 in series, with 7 gradient antibody solutions obtained for each antibody. The 7 gradient antibody solutions for each antibody and the blank PBS control (50 μl per well) were respectively added into the blocked 96-well ELISA plate for incubation at room temperature for 10 minutes.

4) Incubation with Ligand 0.6 μg/ml of PD-L1-mIgG2aFc solution in 50 μl per well was added for incubation at 37° C. for 1 hour.

5) Incubation with Secondary Antibody

After the 96-well ELISA plate was washed with the PBST buffer for three times and gently patted to dryness, goat anti-mouse IgG-HRP (H+L) as a secondary antibody in 1:5000 dilution (50 μl per well) was added for incubation at 37° C. for 1 hour.

6) Developing

After the 96-well ELISA plate was washed with the PBST buffer for three times and gently patted to dryness again, TMB as a developer in 50 μl per well was added for incubation at room temperature for 5 to 15 minutes.

7) Termination of Developing

2M $H_2SO_4$ solution in 50 μl per well was added to terminate developing.

8) Reading

The absorbance of solution in each well was measured on a microplate reader under a wavelength of 450 nm.

Figure 4:
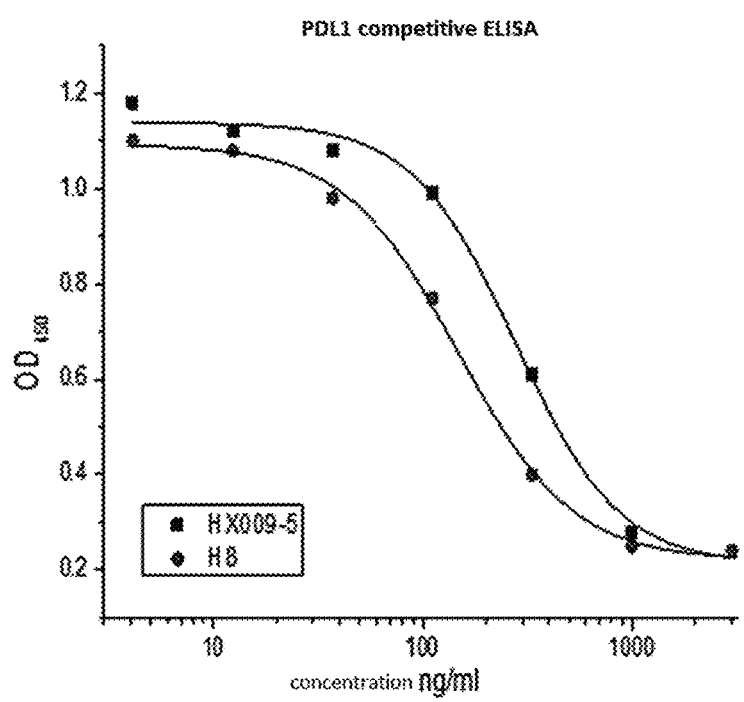
FIG. 4 is a diagram showing results on inhibition of binding between PD-1 and PD-L1 by HX009-5 or H8 according to an embodiment of the present disclosure.

Results are shown in Table 2 and FIG. 4. HX009-5 and H8 antibodies exhibit respective $IC_{50}$ values of 1.5 nM and 1.0 nM, as to inhibition of PD-1 binding to PD-L1, indicating that fusion with Linker-SIRPA (118 mer) at the C-terminus of H8 does not provide the antibody HX009-5 with an obvious change in inhibition of PD-1 binding to PD-L1.

TABLE 2

| Dilution of antibody | HX009-5 | | H8 | |
| --- | --- | --- | --- | --- |
| 3 μg/ml | 0.241 | 0.235 | 0.236 | 0.241 |
| 1:3 | 0.288 | 0.279 | 0.252 | 0.254 |
| 1:9 | 0.618 | 0.607 | 0.403 | 0.398 |
| 1:27 | 1.002 | 0.973 | 0.769 | 0.78 |
| 1:81 | 1.081 | 1.071 | 0.976 | 0.985 |
| 1:243 | 1.108 | 1.141 | 1.064 | 1.09 |
| 1:729 | 1.172 | 1.191 | 1.089 | 1.103 |
| 0 | 1.179 | 1.212 | 0.06 | 0.059 |
| Ligand | PD-L1-mIgG2aFc 0.3 μg/ml | | | |

3. PD-L2 Competitive ELISA Assay of H8 and HX009-5

Specific steps are as below.

1) Antigen Coating

A 96-well ELISA plate was coated with hPD-1-hIgGFc antigen at a concentration of 1.0 μg/ml (100 μl per well) by incubation at 4° C. overnight.

2) Blocking

After washed with the PBST buffer for three times and gently patted to dryness, the coated 96-well ELISA plate was blocked with 1% BSA (diluted in the PBS buffer) at 37° C. for 2 hours, and then washed with 1×PBST buffer containing 1% Tween-20 for four times.

3) Incubation with Primary Antibody

The H8 and HX009-5 antibodies each were diluted from 20 μg/ml by 1:3 in series, with 7 gradient antibody solutions obtained for each antibody. The 7 gradient antibody solutions for each antibody and the blank PBS control (50 μl per well) were respectively added into the blocked 96-well ELISA plate for incubation at room temperature for 10 minutes.

4) Incubation with Ligand 0.6 μg/ml of PD-L2-his tag solution in 50 μl per well was added for incubation at 37° C. for 1 hour.

5) Incubation with secondary antibody

After the 96-well ELISA plate was washed with the PBST buffer for five times and gently patted to dryness, HRP conjugated anti-his tag mouse monoclonal antibody as a secondary antibody in 1:750 dilution (50 μl per well) was added for incubation at 37° C. for 1 hour.

6) Developing

After the 96-well ELISA plate was washed with the PBST buffer for six times and gently patted to dryness again, TMB as a developer in 100 μl per well was added for incubation at room temperature for 30 minutes.

7) Termination of Developing

2M $H_2SO_4$ solution in 50 μl per well was added to terminate developing.

8) Reading

The absorbance of solution in each well was measured on a microplate reader under a wavelength of 450 nm.

Figure 5:
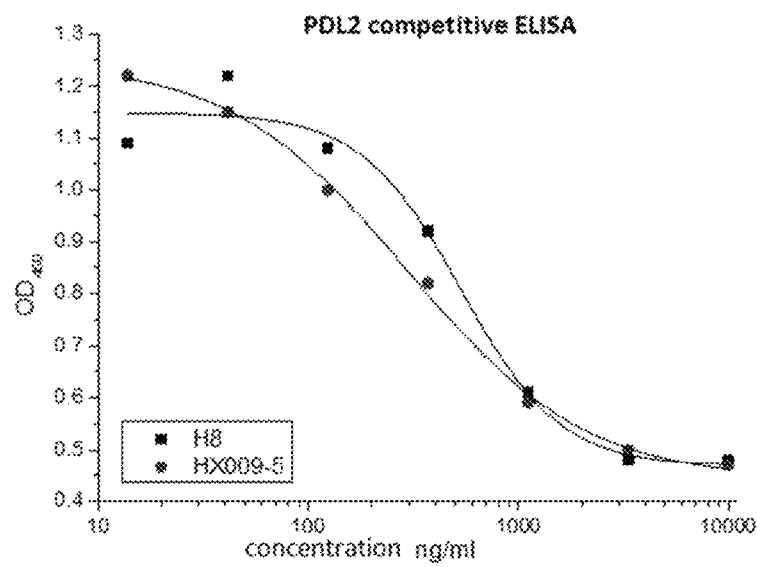
FIG. 5 is a diagram showing results on inhibition of binding between PD-1 and PD-L2 by HX009-5 or H8 according to an embodiment of the present disclosure.

Results are shown in Table 3 and FIG. 5. HX009-5 and H8 exhibit respective $IC_{50}$ values of 1.5 nM and 2.7 nM, as to inhibition of PD-1 binding to PD-L2, indicating that fusion with Linker-SIRPA (118 mer) at the C-terminus of H8 does not provide the antibody HX009-5 with an obvious change in inhibition of PD-1 binding to PD-L2.

TABLE 3

| Dilution of antibody | HX009-5 | | H8 | |
| --- | --- | --- | --- | --- |
| 10 μg/ml | 0.467 | 0.486 | 0.467 | 0.465 |
| 1:3 | 0.474 | 0.484 | 0.517 | 0.489 |
| 1:9 | 0.618 | 0.595 | 0.561 | 0.613 |
| 1:27 | 0.958 | 0.872 | 0.822 | 0.816 |
| 1:81 | 1.173 | 0.985 | 1.008 | 0.99 |
| 1:243 | 1.229 | 1.21 | 1.157 | 1.135 |
| 1:729 | 1.104 | 1.077 | 1.222 | 1.209 |
| blank | 1.096 | 1.092 | 0.142 | 0.136 |
| ligand | PD-L2-his tag 0.3 μg/ml | | | |

4. CD47 Binding ELISA Assay of HX009-5

The CD47 binding ELISA assay of the HX009-5 antibody obtained in Example 1 was conducted. Details are shown as below.

Specific steps are as below.

1) Antigen Coating

An ELISA plate was coated with CD47 antigen at a concentration of 0.25 μg/ml (100 μl per well) by incubation at 4° C. overnight.

2) Blocking

The ELISA plate coated with the CD47 antigen was blocked with 1% BSA (diluted in the PBS buffer) at 37° C. for 2 hours, and then washed with 1×PBST buffer containing 1% Tween-20 for three times, with gently patting to dryness.

3) Incubation with Primary Antibody

The HX009-5 antibody was diluted from 10 μg/ml by 1:5 in series, with 7 gradient antibody solutions obtained. The 7 gradient antibody solution and the blank PBS control were respectively added into the blocked ELISA plate for incubation at 37° C. for 1 hour.

4) Incubation with Secondary Antibody

After the ELISA plate was washed with the PBST buffer for three times and gently patted to dryness, goat anti-human IgG-HRP (H+L) as a secondary antibody in 1:10000 dilution (100 μl per well) was added for incubation at 37° C. for 1 hour.

5) Developing

After the ELISA plate was washed with the PBST buffer for three times and gently patted to dryness again, TMB as a developer in 100 μl per well was added for incubation at room temperature for 5 to 15 minutes.

6) Termination of Developing

2M $H_2SO_4$ solution in 50 μl per well was added to terminate developing.

7) Reading

The absorbance of solution in each well was measured on a microplate reader under a wavelength of 450 nm.

Figure 6:
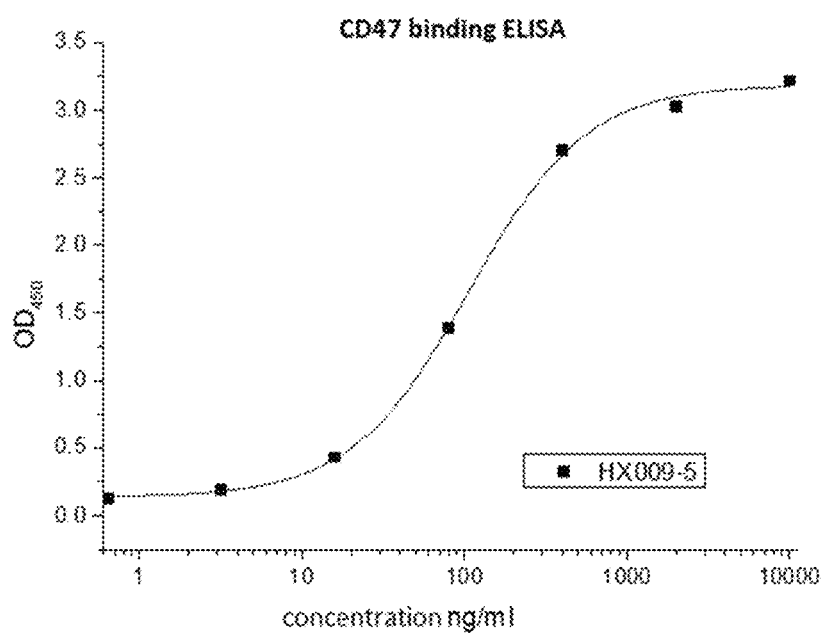
FIG. 6 is a diagram showing experimental results on binding between HX009-5 and hCD47 according to an embodiment of the present disclosure.

Results are shown in Table 4 and FIG. 6. $EC_{50}$ for binding between HX009-5 and hCD47 is 0.6 nM.

TABLE 4

| Dilution of antibody | HX009-5 | |
|---|---|---|
| 10 μg/ml | 3.228 | 3.209 |
| 1:5 | 2.999 | 3.07 |
| 1:25 | 2.791 | 2.61 |
| 1:125 | 1.574 | 1.211 |
| 1:625 | 0.461 | 0.391 |
| 1:3125 | 0.219 | 0.162 |
| 1:15625 | 0.138 | 0.114 |
| 0 | 0.101 | 0.11 |

5. SIPRA competitive ELISA assay of HX009-5

Specific steps are as below.

1) Antigen Coating

A 96-well ELISA plate was coated with CD47 antigen at a concentration of 0.25 μg/ml (100 μl per well) by incubation at 4° C. overnight.

2) Blocking

After washed with the PBST buffer for three times and gently patted to dryness, the coated 96-well ELISA plate was blocked with 1% BSA (diluted in the PBS buffer) at 37° C. for 2 hours, and washed with 1×PBST buffer containing 1% Tween-20 for four times.

3) Incubation with Primary Antibody

The HX009-5 antibody was diluted from 30 μg/ml by 1:3 in series, with 7 gradient antibody solutions obtained. The 7 gradient antibody solutions and the blank PBS control (50 μl per well) were respectively added into the blocked 96-well ELISA plate for incubation at room temperature for 10 minutes.

4) Incubation with Ligand 0.6 μg/ml of SIRPA-his tag solution in 50 μl per well was added for incubation at 37° C. for 1 hour.

5) Incubation with Secondary Antibody

After the 96-well ELISA plate was washed with the PBST buffer for five times and gently patted to dryness, HRP conjugated anti-his tag mouse monoclonal antibody as a secondary antibody in 1:750 dilution (50 μl per well) was added for incubation at 37° C. for 1 hour.

6) Developing

After the 96-well ELISA plate was washed with the PBST buffer for six times and gently patted to dryness again, TMB as a developer in 100 μl per well was added for incubation at room temperature for 30 minutes.

7) Termination of Developing

2M $H_2SO_4$ solution in 50 μl per well was added to terminate developing.

8) Reading

The absorbance of solution in each well was measured on a microplate reader under a wavelength of 450 nm.

Figure 7:
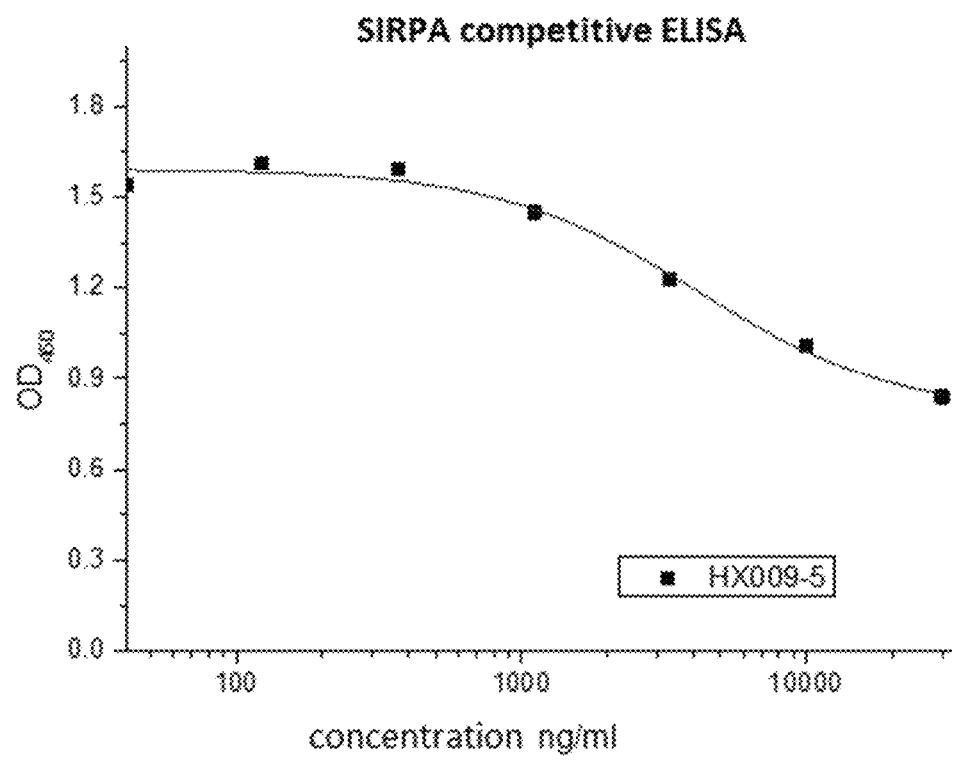
FIG. 7 is a diagram showing experimental results on inhibition of binding between CD47 and SIRPA by HX009-5 according to an embodiment of the present disclosure.

Results shown in Table 5 and FIG. 7 indicate that HX009-5 can inhibit binding between CD47 and SIRPA, with $IC_{50}$ of 21 nM.

TABLE 5

| Dilution of antibody | HX009-5 | |
|---|---|---|
| 10 μg/ml | 3.228 | 3.209 |
| 1:3 | 2.999 | 3.07 |
| 1:9 | 2.791 | 2.61 |
| 1:27 | 1.574 | 1.211 |
| 1:81 | 0.461 | 0.391 |
| 1:243 | 0.219 | 0.162 |
| 1:729 | 0.138 | 0.114 |
| blank | 0.101 | 0.11 |
| ligand | SIRPA-his tag 0.3 μg/ml | |

Example 3 Study on Efficacy of HX009-5 Fc Fragment

To investigate the efficacy of the Fc fragment of HX009-5 (obtained in Example 1), affinities to respective Fc receptors (CD16, CD32a, CD32b and CD64) were assayed, for determination of binding ability of HX009-5 to individual FC receptors. Details are shown as below.

1. Assay on Affinity of HX009-5 to CD16a

The Fc receptor CD16a (also known as FcγRIIIa) can bind to the Fc fragment of IgG antibody, participating in antibody-dependent cell-mediated cytotoxicity (ADCC). The binding capacity between the therapeutic monoclonal antibody and the Fc receptor affects safety and effectiveness of the antibody. In this example, the affinity of HX009-5 to CD16a was assayed by ELISA, so as to evaluate the binding ability of HX009-5 to the Fc receptor CD16a.

The HX009-5 antibody (obtained in Example 1) was detected for binding to CD16a by ELISA in comparison with the HX006 antibody (an IgG1 subtype). Details are shown as below.

Specific steps are as below.

1) Antigen Coating

An ELISA plate was coated with CD16a antigen at a concentration of 0.5 μg/ml (100 μl per well) by incubation at 4° C. overnight.

2) Blocking

The ELISA plate coated with the CD16a antigen was blocked with 1% BSA (diluted in the PBS buffer) at 37° C. for 2 hours, and then washed with 1×PBST buffer containing 1% Tween-20 for three times, with gently patting to dryness.

3) Incubation with Primary Antibody

The HX009-5 antibody was diluted from 10 μg/ml by 1:5 in series, with 7 gradient antibody solutions obtained. The 7 gradient antibody solutions and the blank PBS control were respectively added into the blocked ELISA plate for incubation at 37° C. for 1 hour.

4) Incubation with Secondary Antibody

After the ELISA plate was washed with the PBST buffer for three times and gently patted to dryness, goat anti-human IgG-HRP (H+L) as a secondary antibody in 1:8000 dilution (100 μl per well) was added for incubation at 37° C. for 1 hour.

5) Developing

After the ELISA plate was washed with the PBST buffer for three times and gently patted to dryness again, TMB as a developer in 100 μl per well was added for incubation at room temperature for 30 minutes.

6) Termination of Developing

2M $H_2SO_4$ solution in 50 μl per well was added to terminate developing.

7) Reading

The absorbance of solution in each well was measured on a microplate reader under a wavelength of 450 nm.

Figure 8:
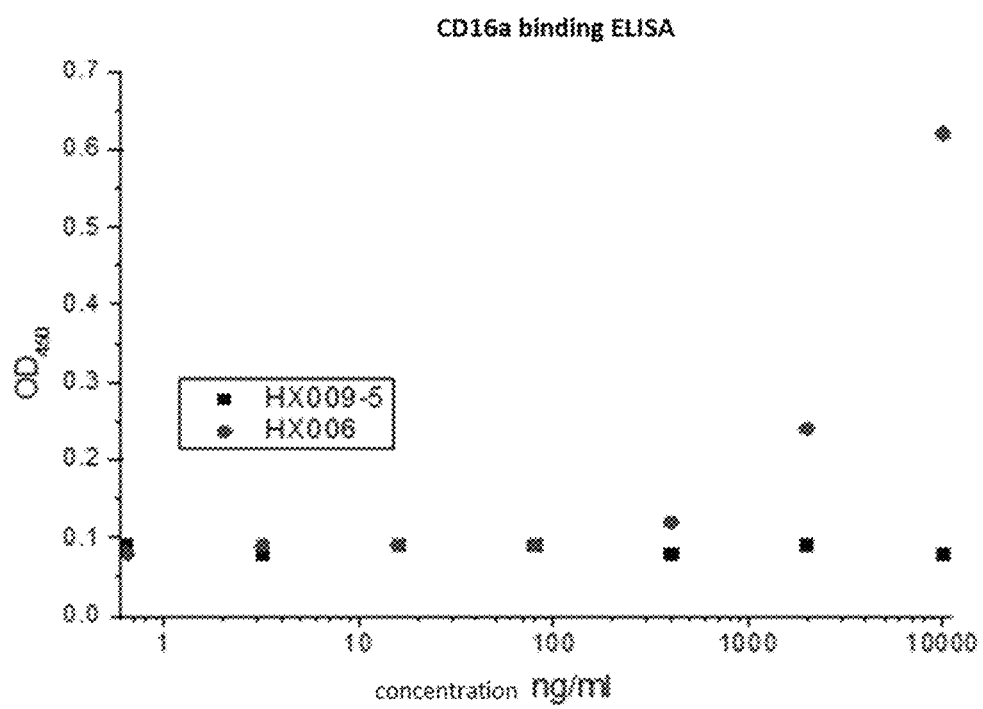
FIG. 8 is a diagram showing experimental results on no binding between HX009-5 and CD16a according to an embodiment of the present disclosure.

Results shown in Table 6 and FIG. 8 indicate no significant binding between HX009-5 and CD16a.

TABLE 6

| Dilution of antibody | HX006 | | HX009-5 | |
|---|---|---|---|---|
| 10 μg/ml | 0.635 | 0.608 | 0.075 | 0.077 |
| 1:5 | 0.254 | 0.218 | 0.089 | 0.092 |
| 1:25 | 0.125 | 0.109 | 0.077 | 0.082 |
| 1:125 | 0.09 | 0.09 | 0.091 | 0.087 |
| 1:625 | 0.096 | 0.086 | 0.09 | 0.096 |
| 1:3125 | 0.087 | 0.087 | 0.083 | 0.084 |
| 1:15625 | 0.085 | 0.079 | 0.087 | 0.086 |
| 0 | 0.079 | 0.076 | 0.075 | 0.08 |

2. Assay on affinity of HX009-5 to CD32a

The HX009-5 antibody (obtained in Example 1) was detected for binding to CD32a by ELISA in comparison with the HX006 antibody (an IgG1 subtype). Details are shown as below.

Specific steps are as below.

1) Antigen Coating

An ELISA plate was coated with CD32a antigen at a concentration of 0.5 μg/ml (100 μl per well) by incubation at 4° C. overnight.

2) Blocking

The ELISA plate coated with the CD32a antigen was blocked with 1% BSA (diluted in the PBS buffer) at 37° C. for 2 hours, and then washed with 1×PBST buffer containing 1% Tween-20 for three times, with gently patting to dryness.

3) Incubation with Primary Antibody

The HX009-5 antibody was diluted from 10 μg/ml by 1:5 in series, with 7 gradient antibody solutions obtained. The 7 gradient antibody solutions and the blank PBS control were respectively added into the blocked ELISA plate for incubation at 37° C. for 1 hour.

4) Incubation with Secondary Antibody

After the ELISA plate was washed with the PBST buffer for three times and gently patted to dryness, goat anti-human IgG-HRP (H+L) as a secondary antibody in 1:8000 dilution (100 μl per well) was added for incubation at 37° C. for 1 hour.

5) Developing

After the ELISA plate was washed with the PBST buffer for three times and gently patted to dryness again, TMB as a developer in 100 μl per well was added for incubation at room temperature for 30 minutes.

6) Termination of Developing

2M $H_2SO_4$ solution in 50 μl per well was added to terminate developing.

7) Reading

The absorbance of solution in each well was measured on a microplate reader under a wavelength of 450 nm.

Figure 9:
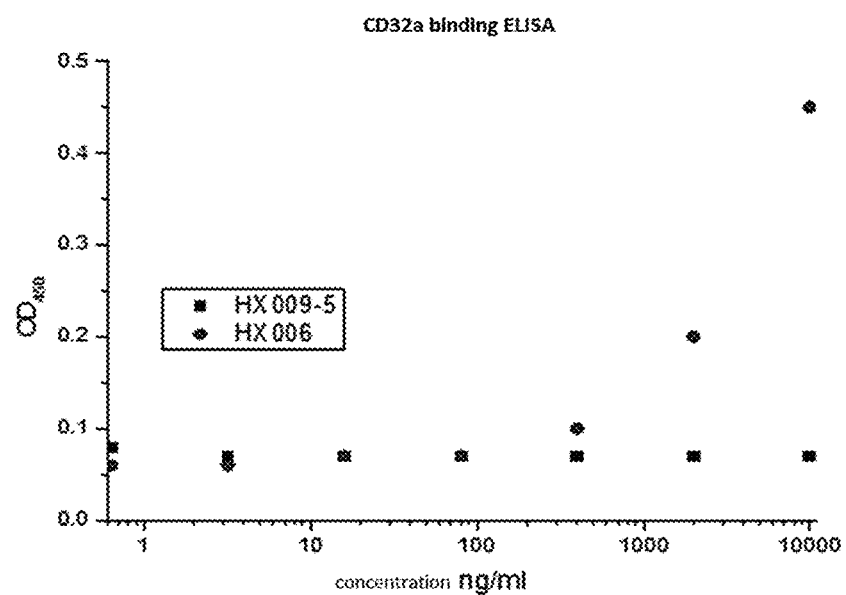
FIG. 9 is a diagram showing experimental results on no binding between HX009-5 and CD32a according to an embodiment of the present disclosure.

Results shown in Table 7 and FIG. 9 indicate no significant binding between HX009-5 and CD32a.

TABLE 7

| Dilution of antibody | HX009-5 | | HX006 | |
|---|---|---|---|---|
| 10 μg/ml | 0.08 | 0.068 | 0.425 | 0.467 |
| 1:5 | 0.08 | 0.068 | 0.193 | 0.207 |
| 1:25 | 0.073 | 0.065 | 0.094 | 0.105 |
| 1:125 | 0.079 | 0.07 | 0.071 | 0.071 |
| 1:625 | 0.074 | 0.068 | 0.065 | 0.069 |
| 1:3125 | 0.074 | 0.064 | 0.062 | 0.065 |
| 1:15625 | 0.083 | 0.071 | 0.065 | 0.064 |
| 0 | 0.073 | 0.072 | 0.068 | 0.071 |

3. Assay on Affinity of HX009-5 to CD32b

The HX009-5 antibody (obtained in Example 1) was detected for binding to CD32b by ELISA in comparison with the HX006 antibody (an IgG1 subtype). Details are shown as below.

Specific steps are as below.

1) Antigen Coating

An ELISA plate was coated with CD32b antigen at a concentration of 0.5 μg/ml (100 μl per well) by incubation at 4° C. overnight.

2) Blocking

The ELISA plate coated with the CD32b antigen was blocked with 1% BSA (diluted in the PBS buffer) at 37° C. for 2 hours, and then washed with 1×PBST buffer containing 1% Tween-20 for three times, with gently patting to dryness.

3) Incubation with Primary Antibody

The HX009-5 antibody was diluted from 10 μg/ml by 1:5 in series, with 7 gradient antibody solutions obtained. The 7 gradient antibody solutions and the blank PBS control were respectively added into the blocked ELISA plate for incubation at 37° C. for 1 hour.

4) Incubation with Secondary Antibody

After the ELISA plate was washed with the PBST buffer for three times and gently patted to dryness, goat anti-human IgG-HRP (H+L) as a secondary antibody in 1:8000 dilution (100 μl per well) was added for incubation at 37° C. for 1 hour.

5) Developing

After the ELISA plate was washed with the PBST buffer for three times and gently patted to dryness again, TMB as a developer in 100 μl per well was added for incubation at room temperature for 30 minutes.

6) Termination of Developing

2M $H_2SO_4$ solution in 50 μl per well was added to terminate developing.

7) Reading

The absorbance of solution in each well was measured on a microplate reader under a wavelength of 450 nm.

Figure 10:
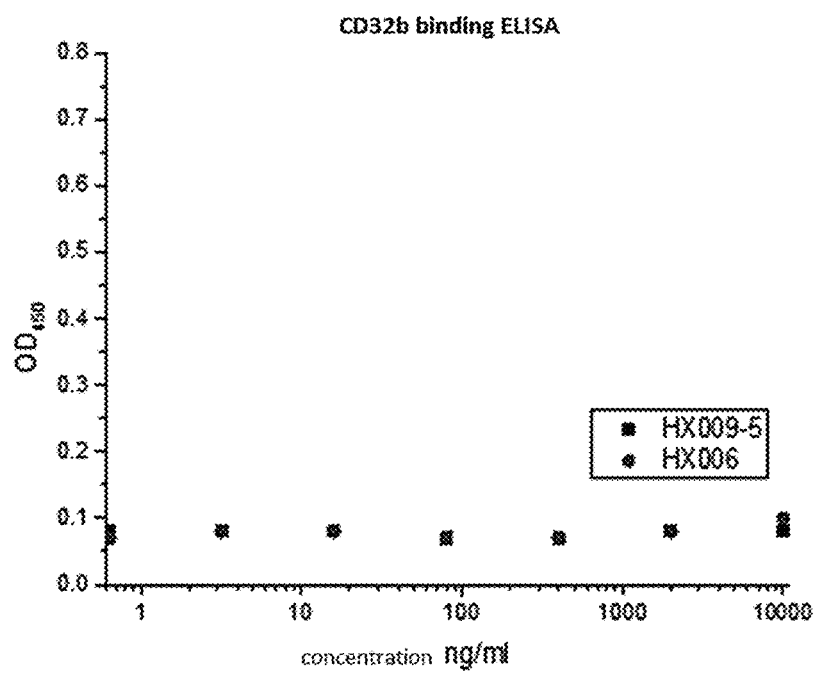
FIG. 10 is a diagram showing experimental results on no binding between HX009-5 and CD32b according to an embodiment of the present disclosure.

Results shown in Table 8 and FIG. 10 indicate no significant binding between HX009-5 and CD32b.

TABLE 8

| Dilution of antibody | HX006 | | HX009-5 | |
|---|---|---|---|---|
| 10 μg/ml | 0.098 | 0.093 | 0.083 | 0.081 |
| 1:5 | 0.076 | 0.074 | 0.078 | 0.072 |
| 1:25 | 0.074 | 0.072 | 0.081 | 0.067 |
| 1:125 | 0.073 | 0.072 | 0.076 | 0.071 |
| 1:625 | 0.069 | 0.075 | 0.094 | 0.07 |

TABLE 8-continued

| Dilution of antibody | HX006 | | HX009-5 | |
|---|---|---|---|---|
| 1:3125 | 0.075 | 0.075 | 0.081 | 0.075 |
| 1:15625 | 0.074 | 0.074 | 0.077 | 0.074 |
| 0 | 0.07 | 0.072 | 0.081 | 0.071 |

4. Assay on Affinity of HX009-5 to CD64

The HX009-5 antibody (obtained in Example 1) was detected for binding to CD64 by ELISA in comparison with the HX006 antibody (an IgG1 subtype). Details are shown as below.

Specific steps are as below.

1) Antigen Coating

An ELISA plate was coated with CD64 antigen at a concentration of 0.5 μg/ml (100 μl per well) by incubation at 4° C. overnight.

2) Blocking

The ELISA plate coated with the CD64 antigen was blocked with 1% BSA (diluted in the PBS buffer) at 37° C. for 2 hours, and then washed with 1×PBST buffer containing 1% Tween-20 for three times, with gently patting to dryness.

3) Incubation with Primary Antibody

The HX009-5 antibody was diluted from 10 μg/ml by 1:5 in series, with 7 gradient antibody solutions obtained. The 7 gradient antibody solutions and the blank PBS control were respectively added into the blocked ELISA plate for incubation at 37° C. for 1 hour.

4) Incubation with Secondary Antibody

After the ELISA plate was washed with the PBST buffer for three times and gently patted to dryness, goat anti-human IgG-HRP (H+L) as a secondary antibody in 1:8000 dilution (100 μl per well) was added for incubation at 37° C. for 1 hour.

5) Developing

After the ELISA plate was washed with the PBST buffer for three times and gently patted to dryness again, TMB as a developer in 100 μl per well was added for incubation at room temperature for 30 minutes.

6) Termination of Developing

2M $H_2SO_4$ solution in 50 μl per well was added to terminate developing.

7) Reading

The absorbance of solution in each well was measured on a microplate reader under a wavelength of 450 nm.

Figure 11:
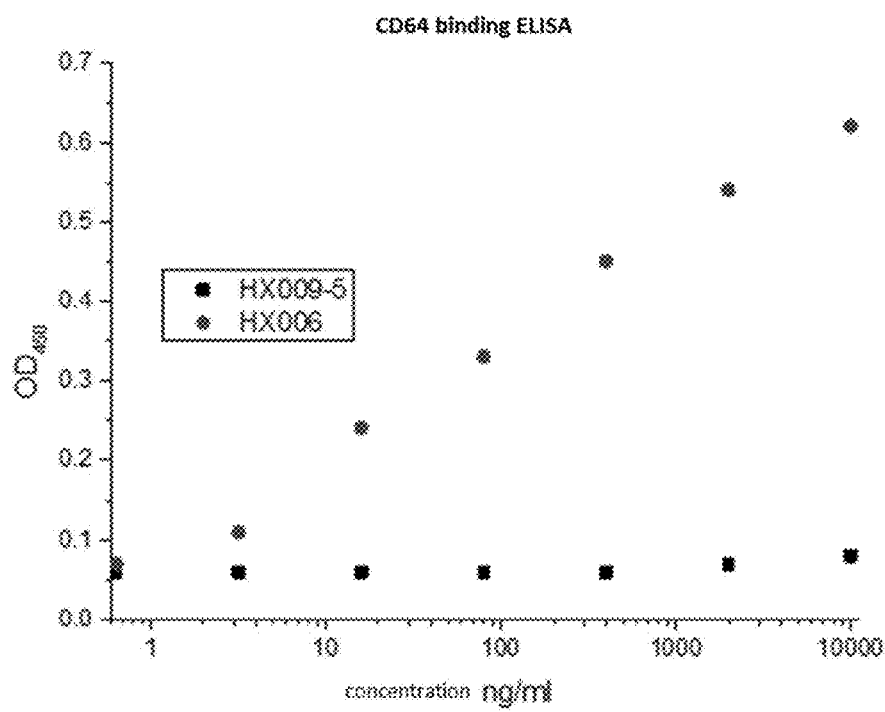
FIG. 11 is a diagram showing experimental results on no binding between HX009-5 and CD64 according to an embodiment of the present disclosure.

Results shown in Table 9 and FIG. 11 indicate no significant binding between HX009-5 and CD64.

TABLE 9

| Dilution of antibody | HX006 | | HX009-5 | |
|---|---|---|---|---|
| 10 μg/ml | 0.623 | 0.616 | 0.085 | 0.08 |
| 1:5 | 0.532 | 0.553 | 0.065 | 0.069 |
| 1:25 | 0.433 | 0.465 | 0.059 | 0.067 |
| 1:125 | 0.329 | 0.33 | 0.058 | 0.061 |
| 1:625 | 0.222 | 0.239 | 0.067 | 0.054 |
| 1:3125 | 0.102 | 0.114 | 0.066 | 0.054 |
| 1:15625 | 0.073 | 0.073 | 0.061 | 0.053 |
| 0 | 0.058 | 0.055 | 0.056 | 0.057 |

Example 4 Biological Activity of the Bi-Specific Antibody and Anti-PD1 Antibody by the Mixed Lymphatic Reaction (MLR)

The ability of stimulating T lymphocytes to secret IL-2 and IFN-gamma was detected between HX009-5 (obtained in Example 1) and H8 by the mixed lymphatic reaction (MLR). Details are shown below.

In the mixed lymphatic reaction, after mixed with dendritic cells (DCs) from a different individual, T cells (TCs) were stimulated to secrete IL-2 and IFN-gamma by DCs presentation. First, monocytes in blood were induced to differentiate into DCs by cytokines GM-CSF and IL-4. The DCs were then stimulated to mature by TNFa. The secretion levels of IL-2 and IFN-gamma in supernatant of cell culture were detected after 5 days of mixing the matured DCs and heterogeneous TCs. In specific, TCs at a concentration of $1×10^5$ cells/well and DCs at a concentration of $1×10^4$ cells/well were mixed in a 96-well plate, where 8 gradient concentrations of antibody from 10 M to 0.09765625 nM were added. After 5 days, the supernatant IL-2 content was quantified using an IL-2 detection kit.

Figure 12:
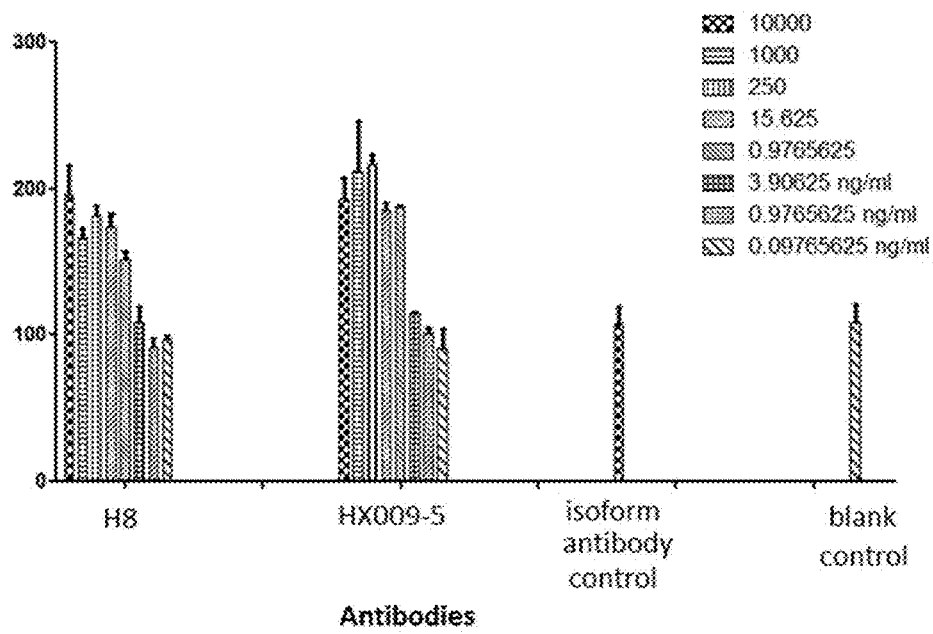
FIG. 12 is a diagram showing experimental results on stimulation of T lymphocytes to secret IL-2 by HX009-5 or H8 according to an embodiment of the present disclosure.

FIG. 12 shows IL-2 secretion levels in T lymphocytes stimulated by respective H8 and HX009-5 antibodies. As can be seen from FIG. 12, H8 and HX009-5 antibodies can effectively stimulate T lymphocytes to secrete IL-2, indicating that fusion with Linker-SIRPA (118 mer) at the C-terminus of H8 does not provide the antibody HX009-5 with any change in stimulating T lymphocytes to secret IL-2.

Example 5 Study on Erythrocyte Agglutination by HX009-5

Specific steps are as follows.

1. From a volunteer, 5 ml peripheral blood was collected into a 5 ml heparin-anticoagulated tube, with sufficient contact by gentle shaking. After transferred to a 15 ml centrifuge tube and mixed with 9 ml PBS under gentle shaking, the peripheral blood was centrifuged at 2100 rpm for 10 min.

2. The supernatant containing white blood cells above the red blood cell layer was discarded, followed by adding 12 ml PBS for re-suspension and then centrifuging at 1500 rpm for 5 min.

3. The supernatant above the red blood cell layer was discarded, followed by adding 12 ml PBS for re-suspension and then centrifuging at 1500 rpm for 5 min.

4. The step 3 was repeated twice.

5. After the supernatant was discarded, 1 ml red blood cell suspension was transferred into a 15 ml centrifuge tube, and mixed with 9 ml PBS to be prepared as 10% red blood cells in PBS ready for use.

6. 1 ml 10% red blood cells in PBS was mixed with 9 ml PBS in a new 15 ml centrifuge tube, thus obtaining 1% red blood cells in PBS ready for use.

7. Preparation of various test samples

1) HX009-5 was diluted from 9.1 mg/ml to 0.9 mg/ml, and then further diluted by 1:3 in series, with 12 gradient concentrations obtained.

2) H8 was diluted from 10 mg/ml to 0.9 mg/ml, and then further diluted by 1:3 in series, with 12 gradient concentrations obtained.

3) The potation lectin extracting solution was diluted by 1:3 in series, with 8 gradient concentrations obtained.

4) PBS was taken as a blank control.

To each well from B1 to G12 in a 96-well U-bottomed plate, added with 50 μl 1% red blood cells in PBS, and 50 μl test samples in a pattern as indicated in the Table 10 below, followed by incubation at 37° C. in a 5% $CO_2$ incubator overnight.

Figure 13:
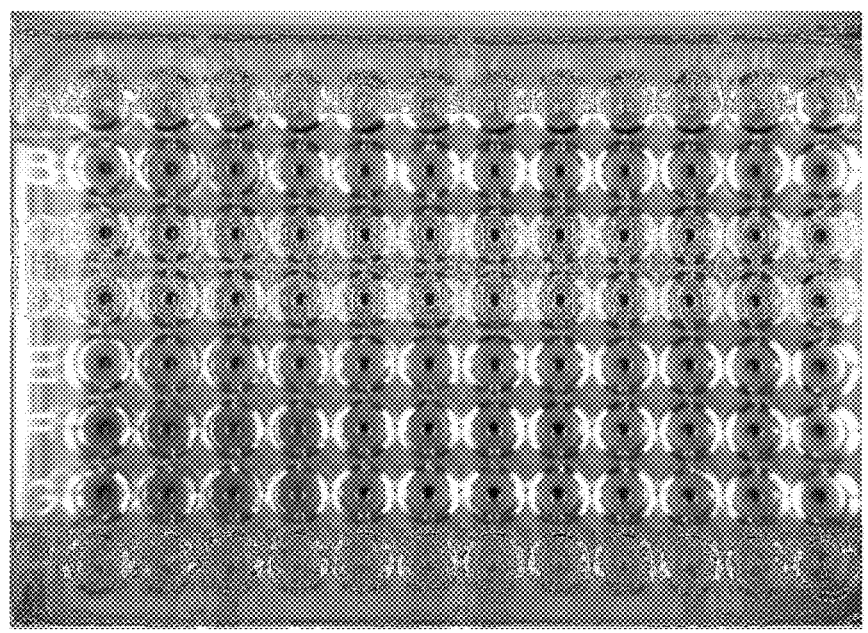
FIG. 13 is a diagram showing experimental results on no erythrocyte agglutination generated by HX009-5 according to an embodiment of the present disclosure.

After 24 hour incubation, the 96-well plate was taken out for observation under a gel imaging analyzer. As shown in Table 10 and FIG. 13, obvious erythrocyte agglutination was observed in the wells added with the potato lectin extracting solutions (as a positive control) at the first 4 concentrations; while no erythrocyte agglutination was observed in the wells added with H8, HX009-5 or PBS at various concentrations, indicating that no erythrocyte agglutination is caused by HX009-5.

TABLE 10

| HX009-5 0.45 mg/ml duplicate | 3x duplicate | 3x duplicate | 3x duplicate | 3x duplicate | 3x duplicate | 3x duplicate | 3x duplicate | 3x duplicate | 3x duplicate | 3x duplicate | 3x duplicate |
|---|---|---|---|---|---|---|---|---|---|---|---|
| H8 0.45 mg/ml duplicate | 3x duplicate | 3x duplicate | 3x duplicate | 3x duplicate | 3x duplicate | 3x duplicate | 3x duplicate | 3x duplicate | 3x duplicate | 3x duplicate | 3x duplicate |
| Potato lectin duplicate | 3x duplicate | 3x duplicate | 3x duplicate | 3x duplicate | 3x duplicate | 3x duplicate | 3x duplicate | PBS PBS | PBS PBS | PBS PBS | PBS PBS |

Example 6 Anti-Tumor Efficacy of HX009-5 on Human Anaplastic Large Cell Lymphoma (KARPAS-299)-Subcutaneously Transplanted Mixeno Model A human tumor-transplanted model was established on a NSG mouse, for study on anti-tumor efficacy of H8 and HX009-5 (obtained in Example 1) on human anaplastic large cell lymphoma (KARPAS-299)-subcutaneously transplanted Mixeno model. Details are shown as below.

The NSG mice, characterized by deficiency/variation of NOD/Prkdcscid/IL2rgnull, are used as a mouse model with the most immune-deficiency that is most suitable for human cell transplantation at present, as almost no rejection exists against human cells and tissues. Thus, the present inventors investigate the in vivo pharmacodynamics of HX009-5 on a graft versus host reaction (GVHD) model established by adoptively introducing human peripheral blood mononuclear cells (PBMCs) to the NSG mice. With the human tumor transplanted model (Mixeno model) based on the NSG mice, the present inventors investigate the anti-tumor efficacy of HX009-5 on human anaplastic large cell lymphoma (KARPAS-299)-subcutaneously transplanted Mixeno model.

On Day 0, KARPAS-299 cells were inoculated subcutaneously into 30 NCG mice at their right backs. On Day 6 from the inoculation when the tumor volume achieved an average value of 60 mm³, 30 NCG mice were divided into 5 groups, with 6 mice in each group. The human peripheral blood mononuclear cells (PBMCs) originated from donor A was transplanted via the tail vein into 3 mice (marked as "A") of each group; while the human peripheral blood mononuclear cells (PBMCs) originated from donor B was transplanted via the tail vein into the rest 3 mice (marked as "B") of each group. The PBMCs from respective donors were suspended in PBS for injection (where the injection volume was 0.1 ml/mouse). To the 5 groups of mice, HX009-5 at individual doses of 0.1 mg/kg, 1 mg/kg and 10 mg/kg, H8 (also indicated as HX008 in the Table 11) at 10 mg/kg as a positive control; and an isoform antibody (Human IgG4) at 5 mg/kg as a control were administered respectively via tail vein for six times at Days 6, 9, 13, 16, 19 and 22 from the inoculation of the tumor cells, as shown in FIG. 11. The therapeutic evaluation was made by the relative tumor suppression rate ($TGI_{RTV}$), and the safety evaluation was made by changes in body weight and mortality.

TABLE 11

Scheme for evaluation of anti-tumor efficacy of HX009-5 on KARPAS-299 Mixeno model

| Group ID | n | PBMC | Administrating Group | Dose (mg/kg) | Route | Volume | Scheme |
|---|---|---|---|---|---|---|---|
| 1 | 3 + 3 | (Day 0) Subcutaneous inoculation Tumor volume 60 mm³ (Day 6 post inoculation of tumor cells) Inoculation of PBMC (i.v.) (100 µL/mouse) | Anti-Hel-hIgG4 | 5 | i.v. | 10 µl/g | Days 6, 9, 13, 16, 19 and 22 post inoculation of tumor cells |
| 2 | 3 + 3 | | HX008 | 10 | i.v. | 10 µl/g | |
| 3 | 3 + 3 | | HX009-5 | 0.1 | i.v. | 10 µl/g | |
| 4 | 3 + 3 | | HX009-5 | 1 | i.v. | 10 µl/g | |
| 5 | 3 + 3 | | HX009-5 | 10 | i.v. | 10 µl/g | |

Note: the drug-administering volume is 10 µl/g; n represents the number of animals; Day 0 is the day that the tumor cells were inoculated; and i.v. represents administration via tail vein.

Figure 14:
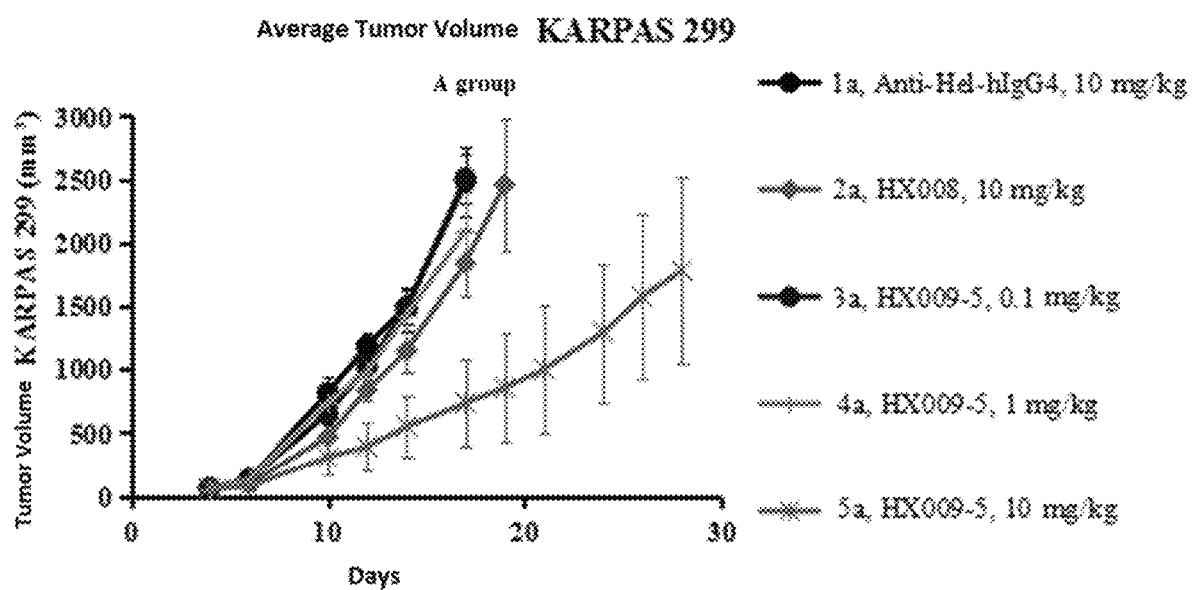
FIG. 14 is a diagram showing results on changes in tumor volumes over times according to an embodiment of the present disclosure.
Figure 15:
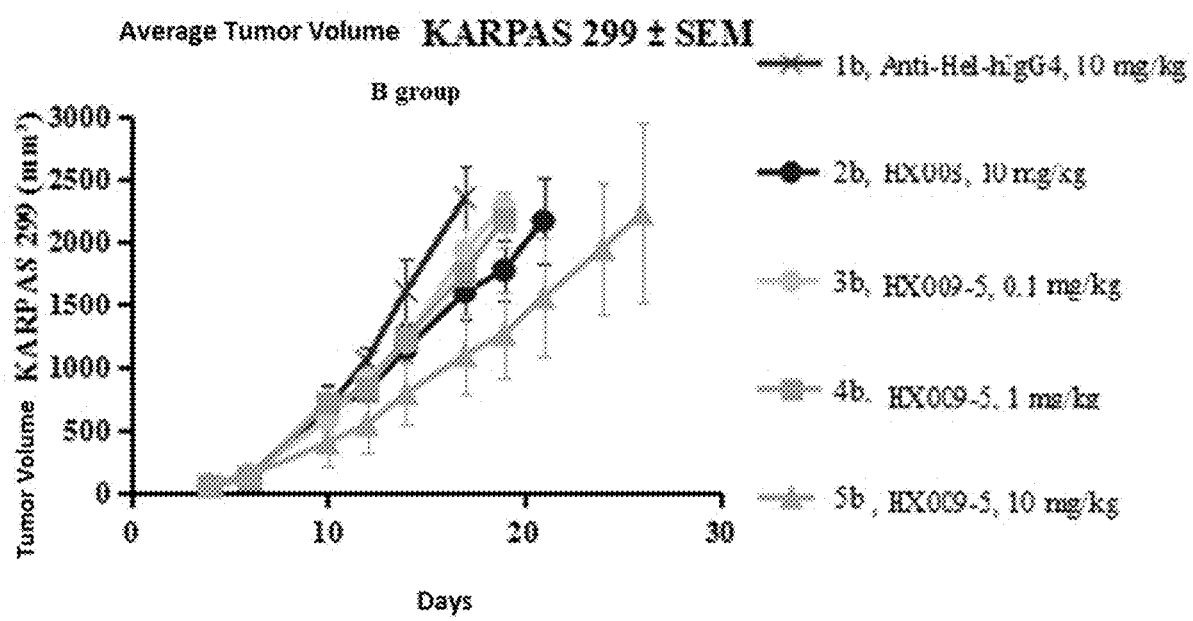
FIG. 15 is a diagram showing results on changes in tumor volumes over times according to an embodiment of the present disclosure.

FIGS. 14 and 15 show changes of tumor volumes in 5 groups over times. Relative to the control group where the PBMCs were inoculated and the isoform antibody (Human IgG4) was administered, administration of HX009-5 or H8 exhibits an obvious anti-tumor efficacy, where dose-dependency was observed for HX009-5, i.e., the higher of the administering dose, the greater of the tumor inhibition. Under the same dose, HX009-5 exhibits more potent anti-tumor efficacy than H8, indicating that the PD1/CD47 dual-target antibody is superior to PD1 single-target antibody.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples", in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments in the scope of the present disclosure.

---

What is claimed is:

1. A recombinant protein, comprising
   a) an anti-PD-1 antibody, and
   b) a human signal regulatory protein α (SIRPA) extracellular segment capable of binding CD47,
   wherein the anti-PD-1 antibody comprises a light chain comprising the amino acid sequence of SEQ ID NO: 2 and a heavy chain comprising the amino acid sequence of SEQ ID NO: 6, and
   wherein the human signal regulatory protein α (SIRPA) extracellular segment having the amino acid sequence of SEQ ID NO: 7, and
   the N-terminus of the human SIRPA extracellular segment is connected to the C-terminus of the heavy chain of the anti-PD-1 antibody by a linker comprising the amino acid sequence of SEQ ID NO: 1.

2. The recombinant protein according to claim 1, wherein the anti-PD-1 antibody is an IgG-like antibody against PD-1.

3. The recombinant protein according to claim 1, wherein the recombinant protein is encoded by a nucleic acid comprising a first nucleotide sequence encoding the light chain of the anti-PD-1 antibody, when combined with the polypeptide, forms an antigen-binding site that binds PD-1; and a second nucleotide sequence encoding the polypeptide.

4. The recombinant protein according to claim 3, wherein the first nucleotide sequence comprises the nucleotide sequence of SEQ ID NO: 4, encoding the light chain of the anti-PD-1 antibody comprising the amino acid sequence of SEQ ID NO: 2, and
   the second nucleotide sequence comprises the nucleotide sequence of SEQ ID NO: 5, encoding the polypeptide comprising the amino acid sequence of SEQ ID NO: 3.

5. The recombinant protein according to claim 1, which is prepared by steps comprising
   introducing a construct into a mammalian cell, and
   culturing the mammalian cell under a condition suitable for protein expression and secretion to obtain the recombinant protein,
   wherein the construct comprises a first nucleic acid molecule encoding the light chain of the anti-PD-1 antibody, when combined with the polypeptide, forms an antigen-binding site that binds PD-1; and a second nucleic acid molecule encoding the polypeptide.

6. The recombinant protein according to claim 5, wherein the construct further comprises a promoter, operably linked to the first nucleic acid molecule,
wherein the promoter is selected from U6, H1, CMV, EF-1, LTR or RSV promoters.

7. The recombinant protein according to claim 6, wherein the vector of the construct is a non-pathogenic viral vector,
wherein the viral vector comprises at least one selected from a retroviral vector, a lentiviral vector or an adenovirus-related viral vector.

8. The recombinant protein according to claim 5, wherein the mammalian cell comprises at least one selected from CHOK1, CHOS, 293F and 293T.

9. A therapeutic composition for treating cancers, comprising the recombinant protein of claim 1 and a pharmaceutically acceptable carrier.

10. A method for treating cancers, comprising administering the recombinant protein of claim 1 to a patient suffered from cancer.

* * * * *